United States Patent
Valencia et al.

(10) Patent No.: US 9,874,396 B2
(45) Date of Patent: Jan. 23, 2018

(54) METHOD AND DEVICE FOR SEPARATING HYDROCARBONS AND CONTAMINANTS WITH A HEATING MECHANISM TO DESTABILIZE AND/OR PREVENT ADHESION OF SOLIDS

(71) Applicants: Jaime A. Valencia, Houston, TX (US); Harry W. Deckman, Clinton, NJ (US); Charles J. Mart, Baton Rouge, LA (US); James T. Wilkins, Houston, TX (US); Paul Scott Northrop, Spring, TX (US)

(72) Inventors: Jaime A. Valencia, Houston, TX (US); Harry W. Deckman, Clinton, NJ (US); Charles J. Mart, Baton Rouge, LA (US); James T. Wilkins, Houston, TX (US); Paul Scott Northrop, Spring, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 546 days.

(21) Appl. No.: 14/516,726

(22) Filed: Oct. 17, 2014

(65) Prior Publication Data

US 2015/0159947 A1    Jun. 11, 2015

Related U.S. Application Data

(60) Provisional application No. 61/912,986, filed on Dec. 6, 2013.

(51) Int. Cl.
*F25J 3/00* (2006.01)
*F25J 3/06* (2006.01)
(Continued)

(52) U.S. Cl.
CPC ............... *F25J 3/067* (2013.01); *B01D 3/42* (2013.01); *C07C 7/05* (2013.01); *C10L 3/104* (2013.01);
(Continued)

(58) Field of Classification Search
CPC ......... Y02C 10/12; C10L 3/102; C10L 3/104; F25J 2205/20; F25J 2280/40;
(Continued)

(56) References Cited

U.S. PATENT DOCUMENTS

| 2,621,216 A | 12/1952 | White | 260/683.3 |
| 2,843,219 A | 7/1958 | Habgood | 183/114.2 |

(Continued)

FOREIGN PATENT DOCUMENTS

| CN | 1151011 | 6/1997 |
| CN | 102803881 | 11/2012 |

(Continued)

OTHER PUBLICATIONS

U.S. Appl. No. 14/516,686, filed Oct. 17, 2014, Valencia, J. A.
(Continued)

*Primary Examiner* — Keith Raymond
(74) *Attorney, Agent, or Firm* — ExxonMobil Upstream Research Company—Law Department

(57) ABSTRACT

The present disclosure provides a method for separating a feed stream in a distillation tower which includes separating a feed stream in a stripper section into an enriched contaminant bottom liquid stream and a freezing zone vapor stream; contacting the freezing zone vapor stream in the controlled freeze zone section with a freezing zone liquid stream at a temperature and pressure at which a solid and a hydrocarbon-enriched vapor stream form; directly applying heat to a controlled freeze zone wall of the controlled freeze zone section with a heating mechanism coupled to at least one of (Continued)

a controlled freeze zone internal surface of the controlled freeze zone wall and a controlled freeze zone external surface of the controlled freeze zone wall; and at least one of destabilizing and preventing adhesion of the solid to the controlled freeze zone wall with the heating mechanism.

26 Claims, 6 Drawing Sheets

(51) Int. Cl.
*C10L 3/10* (2006.01)
*F25J 3/02* (2006.01)
*B01D 3/42* (2006.01)
*C07C 7/05* (2006.01)
*F25J 1/00* (2006.01)
*F25J 3/08* (2006.01)

(52) U.S. Cl.
CPC ............ *F25J 1/0022* (2013.01); *F25J 3/0209* (2013.01); *F25J 3/0233* (2013.01); *F25J 3/0266* (2013.01); *F25J 3/061* (2013.01); *F25J 3/0635* (2013.01); *F25J 3/08* (2013.01); *C10L 3/102* (2013.01); *C10L 3/107* (2013.01); *C10L 2290/543* (2013.01); *C10L 2290/545* (2013.01); *C10L 2290/58* (2013.01); *C10L 2290/60* (2013.01); *F25J 2200/02* (2013.01); *F25J 2200/30* (2013.01); *F25J 2200/50* (2013.01); *F25J 2200/74* (2013.01); *F25J 2205/04* (2013.01); *F25J 2205/20* (2013.01); *F25J 2220/66* (2013.01); *F25J 2235/60* (2013.01); *F25J 2280/02* (2013.01); *F25J 2280/40* (2013.01); *F25J 2290/12* (2013.01); *F25J 2290/40* (2013.01); *Y02C 10/12* (2013.01)

(58) Field of Classification Search
CPC .. F25J 2200/02; F25J 2200/50; F25J 2200/74; F25J 2280/02; F25J 2280/20; F25J 3/0209; F25J 3/0233; F25J 3/061; F25J 3/0635; F25J 3/08; F25J 3/0266; F25J 3/067
See application file for complete search history.

(56) References Cited

U.S. PATENT DOCUMENTS

| | | | |
|---|---|---|---|
| 2,863,527 A | 12/1958 | Herbert et al. ................ 183/115 |
| 2,960,837 A | 11/1960 | Swenson et al. ................ 62/24 |
| 3,050,950 A | 8/1962 | Karwat et al. ................ 62/13 |
| 3,109,726 A | 11/1963 | Karwat ................ 62/13 |
| 3,325,376 A * | 6/1967 | Eckert ................ B01D 3/00 202/100 |
| 3,349,571 A | 10/1967 | Nebgen ................ 62/23 |
| 3,393,527 A | 7/1968 | Swensen et al. ................ 62/16 |
| 3,400,512 A | 9/1968 | McKay ................ 55/69 |
| 3,421,984 A | 1/1969 | Jensen et al. ................ 203/41 |
| 3,683,634 A | 8/1972 | Streich ................ 62/29 |
| 3,705,625 A | 12/1972 | Whitten et al. ................ 166/252 |
| 3,767,766 A | 10/1973 | Tjoa et al. ................ 423/220 |
| 3,824,080 A | 7/1974 | Smith et al. ................ 23/288 |
| 3,842,615 A | 10/1974 | Reigel et al. ................ 62/171 |
| 3,848,427 A | 11/1974 | Loofbourow ................ 62/260 |
| 3,895,101 A | 7/1975 | Tsuruta ................ 423/574 |
| 3,929,635 A | 12/1975 | Buriks et al. ................ 210/54 |
| 3,933,001 A | 1/1976 | Muska ................ 62/47 |
| 4,129,626 A | 12/1978 | Mellbom ................ 261/114 |
| 4,246,015 A | 1/1981 | Styring ................ 62/12 |
| 4,270,937 A | 6/1981 | Adler ................ 62/17 |
| 4,280,559 A | 7/1981 | Best ................ 166/303 |
| 4,281,518 A | 8/1981 | Muller et al. ................ 62/12 |
| 4,318,723 A | 3/1982 | Holmes et al. ................ 62/20 |
| 4,319,964 A | 3/1982 | Katz et al. ................ 202/172 |
| 4,336,233 A | 6/1982 | Appl et al. ................ 423/228 |
| 4,344,485 A | 8/1982 | Butler ................ 166/271 |
| 4,370,156 A | 1/1983 | Goddin et al. ................ 62/17 |
| 4,382,912 A | 5/1983 | Madgavkar et al. ................ 423/224 |
| 4,383,841 A | 5/1983 | Ryan et al. ................ 62/17 |
| 4,405,585 A | 9/1983 | Sartori et al. ................ 423/228 |
| 4,417,449 A | 11/1983 | Hegarty et al. ................ 62/28 |
| 4,417,909 A | 11/1983 | Weltmer ................ 62/12 |
| 4,421,535 A | 12/1983 | Mehra ................ 62/17 |
| 4,441,900 A | 4/1984 | Swallow ................ 62/29 |
| 4,444,577 A | 4/1984 | Perez |
| 4,456,461 A | 6/1984 | Perez |
| 4,459,142 A | 7/1984 | Goddin ................ 62/17 |
| 4,462,814 A | 7/1984 | Holmes et al. ................ 62/17 |
| 4,466,946 A | 8/1984 | Goddin et al. ................ 423/228 |
| 4,511,382 A | 4/1985 | Valencia et al. ................ 62/20 |
| 4,512,782 A | 4/1985 | Bauer et al. ................ 55/48 |
| 4,533,372 A | 8/1985 | Valencia et al. ................ 62/12 |
| 4,551,158 A | 11/1985 | Wagner et al. ................ 55/46 |
| 4,563,202 A | 1/1986 | Yao et al. ................ 62/17 |
| 4,592,766 A | 6/1986 | Kumman et al. ................ 62/18 |
| 4,602,477 A | 7/1986 | Lucadamo ................ 62/24 |
| 4,609,388 A | 9/1986 | Adler et al. ................ 62/12 |
| 4,636,334 A | 1/1987 | Skinner et al. ................ 252/377 |
| 4,695,672 A | 9/1987 | Bunting ................ 585/867 |
| 4,697,642 A | 10/1987 | Vogel ................ 166/263 |
| 4,710,213 A | 12/1987 | Sapper et al. ................ 62/28 |
| 4,717,408 A | 1/1988 | Hopewell ................ 62/20 |
| 4,720,294 A | 1/1988 | Lucadamo et al. ................ 62/31 |
| 4,747,858 A | 5/1988 | Gottier ................ 62/17 |
| 4,761,167 A | 8/1988 | Nicholas et al. ................ 62/17 |
| 4,762,543 A | 8/1988 | Pantermuehl et al. ................ 62/28 |
| 4,769,054 A | 9/1988 | Steigman ................ 62/12 |
| 4,822,393 A | 4/1989 | Markbreiter et al. ................ 62/17 |
| 4,831,206 A | 5/1989 | Zarchy ................ 585/737 |
| 4,923,493 A | 5/1990 | Valencia et al. ................ 62/13 |
| 4,927,498 A | 5/1990 | Rushmere ................ 162/168.3 |
| 4,935,043 A | 6/1990 | Blanc et al. ................ 62/20 |
| 4,954,220 A | 9/1990 | Rushmere ................ 162/168.3 |
| 4,972,676 A | 11/1990 | Sakai ................ 62/18 |
| 4,976,849 A | 12/1990 | Soldati ................ 208/351 |
| 5,011,521 A | 4/1991 | Gottier ................ 62/11 |
| 5,062,270 A | 11/1991 | Haut et al. ................ 62/12 |
| 5,120,338 A | 6/1992 | Potts et al. ................ 62/12 |
| 5,137,550 A | 8/1992 | Hegarty et al. ................ 55/43 |
| 5,152,927 A | 10/1992 | Rivers ................ 252/344 |
| 5,233,837 A | 8/1993 | Callahan ................ 62/38 |
| 5,240,472 A | 8/1993 | Sircar ................ 95/52 |
| 5,247,087 A | 9/1993 | Rivers ................ 544/357 |
| 5,265,428 A | 11/1993 | Valencia et al. ................ 62/36 |
| 5,335,504 A | 8/1994 | Durr et al. ................ 62/20 |
| 5,345,771 A | 9/1994 | Dinsmore ................ 62/18 |
| 5,567,396 A | 10/1996 | Perry et al. ................ 422/190 |
| 5,590,543 A | 1/1997 | Agrawal et al. |
| 5,620,144 A | 4/1997 | Strock et al. ................ 239/557 |
| 5,643,460 A | 7/1997 | Marble et al. ................ 210/705 |
| 5,700,311 A | 12/1997 | Spencer ................ 95/236 |
| 5,720,929 A | 2/1998 | Minkkinen et al. ................ 422/190 |
| 5,819,555 A | 10/1998 | Engdahl ................ 62/637 |
| 5,820,837 A | 10/1998 | Marjanovich et al. ................ 423/220 |
| 5,899,274 A | 5/1999 | Frauenfeld et al. ................ 166/401 |
| 5,956,971 A | 9/1999 | Cole et al. ................ 62/623 |
| 5,964,985 A | 10/1999 | Wootten ................ 201/40 |
| 5,983,663 A | 11/1999 | Sterner ................ 62/620 |
| 6,053,007 A | 4/2000 | Victory et al. ................ 62/619 |
| 6,053,484 A | 4/2000 | Fan et al. ................ 261/114.1 |
| 6,082,133 A | 7/2000 | Barclay et al. ................ 62/619 |
| 6,082,373 A | 7/2000 | Sakurai et al. ................ 134/1 |
| 6,162,262 A | 12/2000 | Minkkinen et al. ................ 23/295 |
| 6,223,557 B1 | 5/2001 | Cole ................ 62/613 |
| 6,240,744 B1 | 6/2001 | Agrawal et al. ................ 62/643 |
| 6,267,358 B1 | 7/2001 | Gohara et al. ................ 261/110 |
| 6,270,557 B1 | 8/2001 | Millet et al. ................ 95/96 |
| 6,274,112 B1 | 8/2001 | Moffett et al. ................ 423/338 |
| 6,336,334 B1 | 1/2002 | Minkkinen et al. ................ 62/123 |
| 6,374,634 B2 | 4/2002 | Gallarda et al. ................ 62/620 |
| 6,401,486 B1 | 6/2002 | Lee et al. ................ 62/630 |

(56) References Cited

U.S. PATENT DOCUMENTS

| | | | |
|---|---|---|---|
| 6,416,729 B1 | 7/2002 | DeBerry et al. | 423/573.1 |
| 6,442,969 B1 | 9/2002 | Rojey et al. | 62/618 |
| 6,500,982 B1 | 12/2002 | Hale et al. | 562/600 |
| 6,505,683 B2 | 1/2003 | Minkkinen et al. | 166/266 |
| 6,516,631 B1 | 2/2003 | Trebble | 62/630 |
| 6,517,801 B2 | 2/2003 | Watson et al. | 423/574.1 |
| 6,539,747 B2 | 4/2003 | Minta et al. | 62/620 |
| 6,565,629 B1 | 5/2003 | Hayashida et al. | 95/211 |
| 6,605,138 B2 | 8/2003 | Frondorf | 95/160 |
| 6,631,626 B1 | 10/2003 | Hahn | 62/612 |
| 6,632,266 B2 | 10/2003 | Thomas et al. | 95/49 |
| 6,662,872 B2 | 12/2003 | Gutek et al. | 166/272.4 |
| 6,708,759 B2 | 3/2004 | Leaute et al. | 166/272.4 |
| 6,711,914 B2 | 3/2004 | Lecomte | 62/625 |
| 6,735,979 B2 | 5/2004 | Lecomte et al. | 62/611 |
| 6,755,251 B2 | 6/2004 | Thomas et al. | 166/265 |
| 6,755,965 B2 | 6/2004 | Pironti et al. | 208/347 |
| 6,818,194 B2 | 11/2004 | DeBerry et al. | 423/228 |
| 6,883,327 B2 | 4/2005 | Iijima et al. | 60/649 |
| 6,946,017 B2 | 9/2005 | Leppin et al. | 95/139 |
| 6,958,111 B2 | 10/2005 | Rust et al. | 202/158 |
| 6,962,061 B2 | 11/2005 | Wilding et al. | 62/613 |
| 7,001,490 B2 | 2/2006 | Wostbrock et al. | 203/1 |
| 7,004,985 B2 | 2/2006 | Wallace et al. | 48/198.3 |
| 7,066,986 B2 | 6/2006 | Haben et al. | 95/99 |
| 7,073,348 B2 | 7/2006 | Clodic et al. | 62/532 |
| 7,121,115 B2 | 10/2006 | Lemaire et al. | 62/625 |
| 7,128,150 B2 | 10/2006 | Thomas et al. | 166/266 |
| 7,128,276 B2 | 10/2006 | Nilsen et al. | 236/124 |
| 7,152,431 B2 | 12/2006 | Amin et al. | 62/637 |
| 7,211,128 B2 | 5/2007 | Thomas et al. | 95/135 |
| 7,211,701 B2 | 5/2007 | Muller et al. | 568/853 |
| 7,219,512 B1 | 5/2007 | Wilding et al. | 62/617 |
| 7,285,225 B2 | 10/2007 | Copeland et al. | 210/785 |
| 7,325,415 B2 | 2/2008 | Amin et al. | 62/541 |
| 7,424,808 B2 | 9/2008 | Mak | 62/625 |
| 7,437,889 B2 | 10/2008 | Roberts et al. | 62/619 |
| 7,442,231 B2 | 10/2008 | Landrum | 95/45 |
| 7,442,233 B2 | 10/2008 | Mitariten | 95/123 |
| 7,493,779 B2 | 2/2009 | Amin | 62/617 |
| 7,536,873 B2 | 5/2009 | Nohlen | 62/644 |
| 7,550,064 B2 | 6/2009 | Bassler et al. | 203/29 |
| 7,575,624 B2 | 8/2009 | Cartwright et al. | 95/51 |
| 7,597,746 B2 | 10/2009 | Mak et al. | 95/169 |
| 7,635,408 B2 | 12/2009 | Mak et al. | 95/187 |
| 7,637,984 B2 | 12/2009 | Adamopoulos | 95/45 |
| 7,637,987 B2 | 12/2009 | Mak | 95/160 |
| 7,641,717 B2 | 1/2010 | Gal | 95/187 |
| 7,662,215 B2 | 2/2010 | Sparling et al. | 95/172 |
| 7,691,239 B2 | 4/2010 | Kister et al. | 203/2 |
| 7,722,289 B2 | 5/2010 | Leone et al. | 405/53 |
| 7,729,976 B2 | 6/2010 | Hill et al. | 705/37 |
| 7,770,872 B2 | 8/2010 | Delatour | 261/110 |
| 7,795,483 B2 | 9/2010 | Kulprathipanja et al. | 585/24 |
| 7,806,965 B2 | 10/2010 | Stinson | 95/187 |
| 7,814,975 B2 | 10/2010 | Hagen et al. | 166/257 |
| 7,879,135 B2 | 2/2011 | Ravikumar et al. | 95/11 |
| 7,901,583 B2 | 3/2011 | McColl et al. | 210/710 |
| 7,955,496 B2 | 6/2011 | Iqbal et al. | 208/129 |
| 8,002,498 B2 | 8/2011 | Leone et al. | 405/53 |
| 8,020,408 B2 | 9/2011 | Howard et al. | 62/646 |
| 8,133,764 B2 | 3/2012 | Dirks et al. | 438/124 |
| 8,136,799 B2 | 3/2012 | Griepsma | 261/114.5 |
| 8,303,685 B2 | 11/2012 | Schubert et al. | 95/181 |
| 8,308,849 B2 | 11/2012 | Gal | 95/187 |
| 8,312,738 B2 | 11/2012 | Singh et al. | 62/629 |
| 8,372,169 B2 | 2/2013 | Tsangaris et al. | 48/120 |
| 8,381,544 B2 | 2/2013 | Coyle | 62/612 |
| 8,388,832 B2 | 3/2013 | Moffett et al. | 208/390 |
| 8,428,835 B2 | 4/2013 | Habert et al. | 701/54 |
| 8,475,572 B2 | 7/2013 | Prast et al. | 95/269 |
| 8,500,105 B2 | 8/2013 | Nieuwoudt | 261/79.2 |
| 8,529,662 B2 | 9/2013 | Kelley et al. | 95/96 |
| 2002/0174687 A1 | 11/2002 | Cai | 65/158 |
| 2002/0189443 A1 | 12/2002 | McGuire | 95/32 |
| 2003/0181772 A1 | 9/2003 | Meyer et al. | 585/324 |
| 2005/0092594 A1 | 5/2005 | Parro et al. | |
| 2006/0207946 A1 | 9/2006 | McColl et al. | 210/733 |
| 2006/0239879 A1 | 10/2006 | Lallemand et al. | 423/210 |
| 2007/0056317 A1 | 3/2007 | Amin et al. | 62/532 |
| 2007/0144943 A1 | 6/2007 | Lemaire et al. | 208/208 |
| 2007/0277674 A1 | 12/2007 | Hirano et al. | 95/290 |
| 2008/0034789 A1 | 2/2008 | Fieler et al. | 62/623 |
| 2008/0091316 A1 | 4/2008 | Szczublewski | 701/36 |
| 2008/0092589 A1 | 4/2008 | Trainer et al. | 62/640 |
| 2008/0307827 A1 | 12/2008 | Hino et al. | 62/634 |
| 2009/0023605 A1 | 1/2009 | Lebl et al. | 506/27 |
| 2009/0220406 A1 | 9/2009 | Rahman | 423/437.1 |
| 2010/0011809 A1 | 1/2010 | Mak | 62/620 |
| 2010/0018248 A1 | 1/2010 | Fieler et al. | 62/617 |
| 2010/0024472 A1 | 2/2010 | Amin et al. | 62/541 |
| 2010/0064725 A1 | 3/2010 | Chieng et al. | 62/620 |
| 2010/0107687 A1 | 5/2010 | Andrian et al. | 62/620 |
| 2010/0132405 A1 | 6/2010 | Nilsen | 62/611 |
| 2010/0147022 A1 | 6/2010 | Hart et al. | 62/601 |
| 2010/0187181 A1 | 7/2010 | Sortwell | 210/726 |
| 2010/0236285 A1* | 9/2010 | Johnke | C10G 5/06 62/620 |
| 2010/0310439 A1 | 12/2010 | Brok et al. | 423/222 |
| 2011/0132034 A1 | 6/2011 | Beaumont et al. | 62/620 |
| 2011/0154856 A1 | 6/2011 | Andrian et al. | 62/618 |
| 2011/0168019 A1 | 7/2011 | Northrop et al. | 95/186 |
| 2011/0192190 A1 | 8/2011 | Andrian et al. | 62/617 |
| 2011/0265512 A1 | 11/2011 | Bearden et al. | 62/617 |
| 2012/0006055 A1 | 1/2012 | Van Santen et al. | 62/618 |
| 2012/0031143 A1 | 2/2012 | Van Santem et al. | 62/617 |
| 2012/0031144 A1 | 2/2012 | Northrop et al. | 62/617 |
| 2012/0079852 A1 | 4/2012 | Northrop et al. | 62/620 |
| 2012/0125043 A1* | 5/2012 | Cullinane | B01D 7/02 62/620 |
| 2012/0204599 A1 | 8/2012 | Northrop et al. | 62/617 |
| 2012/0279728 A1 | 11/2012 | Northrop et al. | 166/401 |
| 2013/0032029 A1 | 2/2013 | Mak | 95/94 |
| 2013/0074541 A1 | 3/2013 | Kaminsky et al. | 62/601 |
| 2013/0098105 A1 | 4/2013 | Northrop | 62/617 |
| 2014/0137599 A1 | 5/2014 | Oelfke et al. | 62/619 |

FOREIGN PATENT DOCUMENTS

| | | | |
|---|---|---|---|
| DE | 3149847 | 7/1983 | B01D 5/00 |
| EP | 0133208 | 2/1985 | B01D 53/14 |
| EP | 0508244 | 10/1992 | B01D 53/34 |
| EP | 1338557 | 3/2005 | C01B 17/04 |
| GB | 1010403 | 11/1965 | |
| WO | WO 2002/032536 | 4/2002 | B01F 13/00 |
| WO | WO 2002/039038 | 5/2002 | |
| WO | WO 2004/047956 | 6/2004 | B01D 53/14 |
| WO | WO 2008/034789 | 3/2008 | G10K 11/00 |
| WO | WO 2008/095258 | 8/2008 | |
| WO | WO 2008/152030 | 12/2008 | B01D 53/00 |
| WO | WO 2009/023605 | 2/2009 | C10G 21/00 |
| WO | WO 2009/029353 | 3/2009 | E21B 43/00 |
| WO | WO 2009/087206 | 7/2009 | B01D 53/00 |
| WO | WO 2010/023238 | 3/2010 | |
| WO | WO 2010/052299 | 5/2010 | B01D 53/00 |
| WO | WO 2010/096223 | 8/2010 | |
| WO | WO 2010/136442 | 12/2010 | B01D 53/00 |
| WO | WO 2011/026170 | 3/2011 | C10L 3/10 |
| WO | WO 2013/095828 | 6/2013 | B01D 53/00 |
| WO | WO 2013/142100 | 9/2013 | B03C 3/00 |

OTHER PUBLICATIONS

U.S. Appl. No. 14/516,689, filed Oct. 17, 2014, Cullinane, J. T. et al.

U.S. Appl. No. 14/516,705, filed Oct. 17, 2014, Valencia, J. A. et al.

U.S. Appl. No. 14/516,709, filed Oct. 17, 2014, Valencia, J. A.

U.S. Appl. No. 14/516,713, filed Oct. 17, 2014, Valencia, J. A. et al.

U.S. Appl. No. 14/516,717, filed Oct. 17, 2014, Valencia, J. A. et al.

U.S. Appl. No. 14/516,718, filed Oct. 17, 2014, Valencia, J. A.

U.S. Appl. No. 14/516,726, filed Oct. 17, 2014, Valencia, J. A. et al.

U.S. Appl. No. 14/516,731, filed Oct. 17, 2014, Valencia, J. A. et al.

(56) References Cited

OTHER PUBLICATIONS

Aaron, D. et al. (2005) "Separation of $CO_2$ from Flue Gas: A Review," *Separation Science and Technology*, 40, pp. 321-348.

Amin, R. (2003) "Advanced Mini Natural Gas Liquefier," *LNG Journal*, Mar.-Apr. 2003, pp. 20-23.

Black, S. (2006) "Chilled Ammonia Process for CO2 Capture," *Alstom Position Paper*, Nov. 2006, 6 pgs.

Ciulla, Vincent (2007) "How the Engine Works," About.com, Mar. 21, 2007, [retrieved from the internet on Aug. 17, 2012]. <URL: http://autorepair.about.com/cs/generalinfo/a/aa060500a.html>.

"Cryogenics" *Science Clarified*, May 2, 2006 [retrieved from the internet on Aug. 17, 2012]. <URL: http://www.scienceclarified.com/Co-Di/Cryogenics.html>.

Denton, R. D. et al. (1985) "Integrated Low Temperature Processing of Sour Natural Gas," *Gas Processors Assoc.*, $64^{th}$ Ann. Conv., pp. 92-96.

Guccione, E. (1963) "New Approach to Recovery of Helium from Natural Gas," Chem. Engr., Sep. 30, 1963, pp. 76-78.

Hassan, S. M. N. (2005) "Techno-Economic Study of $CO_2$ Capture Process for Cement Plants," *University of Waterloo—Thesis*.

Haut, R. C. et al. (1988) "Development and Application of the Controlled Freeze Zone Process," *SPE 17757, SPE Gas Tech. Symp.—Dallas, TX*, pp. 435-443.

Haut, R. C. et al. (1988) "Development and Application of the Controlled Freeze Zone Process," *OSEA 88197, $7^{th}$ Offshore So. East Asia Conf., Singapore*, Feb. 1988, pp. 840-848.

Haut, R. C. et al. (1989) "Development and Application of the Controlled Freeze Zone Process," *SPE Production Engineering*, Aug. 1989, pp. 265-271.

Im, U. K. et al. (1971) "Heterogeneous Phase Behavior of Carbon Dioxide in n-Hexane and n-Heptane at Low Temperatures," *Jrnl. of Chem. Engineering Data*, v.16.4, pp. 412-415.

Mitariten, M. et al. (2007) "The Sorbead™ Quick-Cycle Process for Simultaneous Removal of Water, Heavy Hydrocarbons and Mercaptans from Natural Gas," *Laurance Reid Gas Conditioning Conf.*, Feb. 25-27, 2007.

Northrop, P. Scott et al. (2004) "Cryogenic Sour Gas Process Attractive for Acid Gas Injection Applications," $83^{rd}$ *Ann. Gas Processors Assoc. Convention, New Orleans, LA.*, pp. 1-8 (XP007912217).

Pagcatipunan, C. et al. (2005) "Maximize the Performance of Spray Nozzle Systems," *CEP Magazine*, Dec. 2005, pp. 38-44.

Reyes, S. C. et al. (1997) "Frequency Modulation Methods for Diffusion and Adsorption Measurements in Porous Solids," *J. Phys. Chem. B*, v.101, pp. 614-622.

Rubin, E. S. et al. (2002) "A Technical, Economic and Environmental Assessment of Amine-based CO2 Capture Technology for Power Plant Greenhouse Gas Control," *U.S. Dept. of Energy*, Oct. 2002, DOE/DE-FC26-00NT40935, 26 pages.

Spero, C. (2007) "Callide Oxyfuel Project," *CS Energy, cLET Seminar*, Jul. 12, 2007, 9 pages.

Thomas, E. R. et al. (1987) "Conceptual Studies Using the Controlled Freeze Zone (CFZ) Process," *AIChE Summer Nat'l Mtg.*, Aug. 16-19, 1987.

Thomas, E. R. et al. (1988) "Conceptual Studies for $CO_2$/Natural Gas Separation Using the Control Freeze Zone (CFZ) Process," *Gas Separation and Purification*, v. 2, pp. 84-89.

Valencia, J. A. et al. (2008) "Controlled Freeze Zone™ Technology for Enabling Processing of High $CO_2$ and $H_2S$ Gas Reserves," SPE-IPTC 12708, Kuala Lumpur, IN, v.4.1, Jan. 2008, pp. 2358-2363.

Victory, D. J. et al. (1987) "The CFZ Process: Direct Methane-Carbon Dioxide Fractionation," $66^{th}$ *Ann. GPA Convention*, Mar. 16-18, Denver, CO.

Wilson, R.W. et al. (1968) "Helium: Its Extraction and Purification," *Journ. Petrol. Tech.*, v. 20, pp. 341-344.

\* cited by examiner

METHOD AND DEVICE FOR SEPARATING HYDROCARBONS AND CONTAMINANTS WITH A HEATING MECHANISM TO DESTABILIZE AND/OR PREVENT ADHESION OF SOLIDS

CROSS REFERENCE TO RELATED APPLICATIONS

This application claims the priority benefit of U.S. patent application No. 61/912,986 filed Dec. 6, 2013 entitled METHOD AND DEVICE FOR SEPARATING HYDROCARBONS AND CONTAMINANTS WITH A HEATING MECHANISM TO DESTABILIZE AND/OR PREVENT ADHESION OF SOLIDS, the entirety of which is incorporated by reference herein.

This application is related to but does not claim priority to U.S. Provisional patent application Nos. 61/912,957 filed Dec. 6, 2013 entitled METHOD AND DEVICE FOR SEPARATING HYDROCARBONS AND CONTAMINANTS WITH A SPRAY ASSEMBLY; 62/044,770 filed Sep. 2, 2014 entitled METHOD AND DEVICE FOR SEPARATING HYDROCARBONS AND CONTAMINANTS WITH A SPRAY ASSEMBLY; 61/912,959 filed on Dec. 6, 2013 entitled METHOD AND SYSTEM OF MAINTAINING A LIQUID LEVEL IN A DISTILLATION TOWER; 61/912,964 filed on Dec. 6, 2013 entitled METHOD AND DEVICE FOR SEPARATING A FEED STREAM USING RADIATION DETECTORS; 61/912,970 filed on Dec. 6, 2013 entitled METHOD AND SYSTEM OF DEHYDRATING A FEED STREAM PROCESSED IN A DISTILLATION TOWER; 61/912,975 filed on Dec. 6, 2013 entitled METHOD AND SYSTEM FOR SEPARATING A FEED STREAM WITH A FEED STREAM DISTRIBUTION MECHANISM; 61/912,978 filed on Dec. 6, 2013 entitled METHOD AND SYSTEM FOR PREVENTING ACCUMULATION OF SOLIDS IN A DISTILLATION TOWER; 61/912,983 filed on Dec. 6, 2013 entitled METHOD OF REMOVING SOLIDS BY MODIFYING A LIQUID LEVEL IN A DISTILLATION TOWER; 61/912,984 filed on Dec. 6, 2013 entitled METHOD AND SYSTEM OF MODIFYING A LIQUID LEVEL DURING START-UP OPERATIONS; 61/912,987 filed on Dec. 6, 2013 entitled METHOD AND DEVICE FOR SEPARATING HYDROCARBONS AND CONTAMINANTS WITH A SURFACE TREATMENT MECHANISM.

BACKGROUND

Fields of Disclosure

The disclosure relates generally to the field of fluid separation. More specifically, the disclosure relates to the cryogenic separation of contaminants, such as acid gas, from a hydrocarbon.

Description of Related Art

This section is intended to introduce various aspects of the art, which may be associated with the present disclosure. This discussion is intended to provide a framework to facilitate a better understanding of particular aspects of the present disclosure. Accordingly, it should be understood that this section should be read in this light, and not necessarily as admissions of prior art.

The production of natural gas hydrocarbons, such as methane and ethane, from a reservoir oftentimes carries with it the incidental production of non-hydrocarbon gases. Such gases include contaminants, such as at least one of carbon dioxide ("$CO_2$"), hydrogen sulfide ("$H_2S$"), carbonyl sulfide, carbon disulfide and various mercaptans. When a feed stream being produced from a reservoir includes these contaminants mixed with hydrocarbons, the stream is oftentimes referred to as "sour gas."

Many natural gas reservoirs have relatively low percentages of hydrocarbons and relatively high percentages of contaminants. Contaminants may act as a diluent and lower the heat content of hydrocarbons. Some contaminants, like sulfur-bearing compounds, are noxious and may even be lethal. Additionally, in the presence of water some contaminants can become quite corrosive.

It is desirable to remove contaminants from a stream containing hydrocarbons to produce sweet and concentrated hydrocarbons. Specifications for pipeline quality natural gas typically call for a maximum of 2-4% $CO_2$ and ¼ grain $H_2S$ per 100 scf (4 ppmv) or 5 mg/Nm3 $H_2S$. Specifications for lower temperature processes such as natural gas liquefaction plants or nitrogen rejection units typically require less than 50 ppm $CO_2$.

The separation of contaminants from hydrocarbons is difficult and consequently significant work has been applied to the development of hydrocarbon/contaminant separation methods. These methods can be placed into three general classes: absorption by solvents (physical, chemical and hybrids), adsorption by solids, and distillation.

Separation by distillation of some mixtures can be relatively simple and, as such, is widely used in the natural gas industry. However, distillation of mixtures of natural gas hydrocarbons, primarily methane, and one of the most common contaminants in natural gas, carbon dioxide, can present significant difficulties. Conventional distillation principles and conventional distillation equipment are predicated on the presence of only vapor and liquid phases throughout the distillation tower. The separation of $CO_2$ from methane by distillation involves temperature and pressure conditions that result in solidification of $CO_2$ if a pipeline or better quality hydrocarbon product is desired. The required temperatures are cold temperatures typically referred to as cryogenic temperatures.

Certain cryogenic distillations can overcome the above mentioned difficulties. These cryogenic distillations provide the appropriate mechanism to handle the formation and subsequent melting of solids during the separation of solid-forming contaminants from hydrocarbons. The formation of solid contaminants in equilibrium with vapor-liquid mixtures of hydrocarbons and contaminants at particular conditions of temperature and pressure takes place in a controlled freeze zone section.

Sometimes solids can adhere to an internal (e.g., controlled freeze zone wall) of the controlled freeze zone section rather than falling to the bottom of the controlled freeze zone section.

The adherence is disadvantageous. The adherence, if uncontrolled, can interfere with the proper operation of the controlled freeze zone and the effective separation of methane from the contaminants.

A need exists for improved technology to destabilize and/or prevent any adhesion of solids to surface(s) in the controlled freeze zone section.

SUMMARY

The present disclosure provides a device and method for separating contaminants from hydrocarbons and destabilizing and/or preventing the adhesion of solids to surface(s) in the controlled freeze section, among other things.

The method for separating a feed stream in a distillation tower comprises introducing a feed stream into one of a stripper section and a controlled freeze zone section of a distillation tower, the feed stream comprising a hydrocarbon and a contaminant; separating the feed stream in the stripper section into an enriched contaminant bottom liquid stream, comprising the contaminant, and a freezing zone vapor stream, comprising the hydrocarbon, at a temperature and pressure at which no solid forms; contacting the freezing zone vapor stream in the controlled freeze zone section with a freezing zone liquid stream, comprising the hydrocarbon, at a temperature and pressure at which a solid, comprising the contaminant forms, and a vapor stream, further enriched in the hydrocarbon emerges; directly applying heat to the controlled freeze zone wall of the controlled freeze zone section with a heating mechanism coupled to at least one of a controlled freeze zone internal surface of the controlled freeze zone wall and a controlled freeze zone external surface of the controlled freeze zone wall; and at least one of destabilizing and preventing adhesion of the solid to the controlled freeze zone wall with the heating mechanism.

The distillation tower that separates a contaminant in a feed stream from a hydrocarbon in the feed stream comprises a stripper section constructed and arranged to separate a feed stream, comprising a contaminant and a hydrocarbon, into an enriched contaminant bottom liquid stream, comprising the contaminant, and a freezing zone vapor stream, comprising the hydrocarbon, at a temperature and pressure at which no solids form; a controlled freeze zone section comprising: a melt tray assembly at a bottom section of the controlled freeze zone section that is constructed and arranged to melt a solid, comprising the contaminant, formed in the controlled freeze zone section; a heating mechanism coupled to at least one of a controlled freeze zone internal surface of a controlled freeze zone wall of the controlled freeze zone section and a controlled freeze zone external surface of the controlled freeze zone wall that at least one of destabilizes and prevents adhesion of the solid to the controlled freeze zone wall, wherein the heating mechanism is in an upper section of the controlled freeze zone section that directly abuts and is separate from the bottom section.

A method for producing hydrocarbons may comprise extracting a feed stream comprising a hydrocarbon and a contaminant from a reservoir; introducing the feed stream into one of a stripper section and a controlled freeze zone section of a distillation tower; separating the feed stream in the stripper section into an enriched contaminant bottom liquid stream, comprising the contaminant, and a freezing zone vapor stream, comprising the hydrocarbon, at a temperature and pressure at which no solid forms; contacting the freezing zone vapor stream in the controlled freeze zone section with a freezing zone liquid stream, comprising the hydrocarbon, at a temperature and pressure at which the freezing zone vapor stream forms a solid, comprising the contaminant, and a hydrocarbon-enriched vapor stream, comprising the hydrocarbon; directly applying heat to a controlled freeze zone wall of the controlled freeze zone section with a heating mechanism coupled to at least one of a controlled freeze zone internal surface of the controlled freeze zone wall and a controlled freeze zone external surface of the controlled freeze zone wall; at least one of destabilizing and preventing adhesion of the solid to the controlled freeze zone wall with the heating mechanism; removing the hydrocarbon-enriched vapor stream from the distillation tower; and producing the hydrocarbon-enriched vapor stream extracted from the distillation tower.

The foregoing has broadly outlined the features of the present disclosure so that the detailed description that follows may be better understood. Additional features will also be described herein.

BRIEF DESCRIPTION OF THE DRAWINGS

These and other features, aspects and advantages of the disclosure will become apparent from the following description, appending claims and the accompanying drawings, which are briefly described below.

Figure 1:
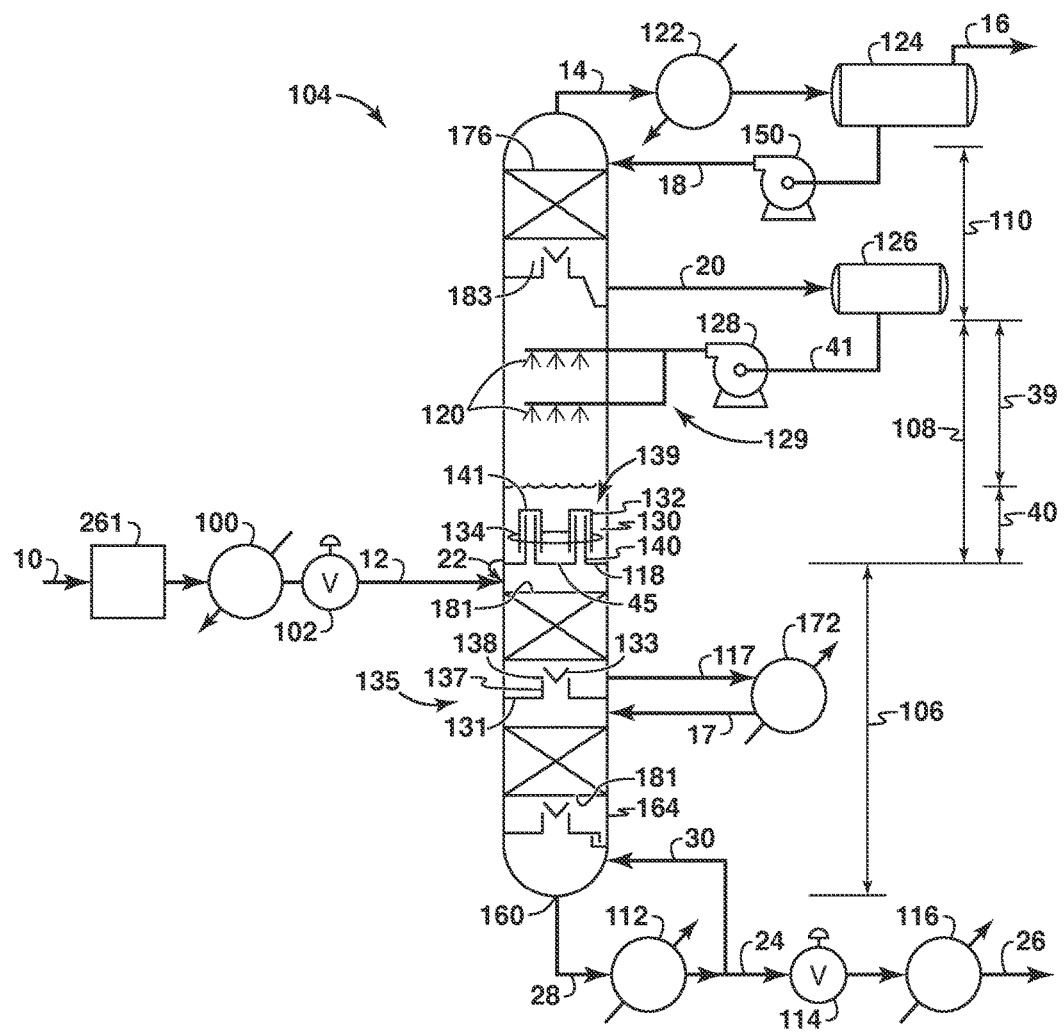
FIG. 1 is a schematic diagram of a tower with sections within a single vessel.

It should be noted that the figures are merely examples and no limitations on the scope of the present disclosure are intended thereby. Further, the figures are generally not drawn to scale, but are drafted for purposes of convenience and clarity in illustrating various aspects of the disclosure.

DETAILED DESCRIPTION

For the purpose of promoting an understanding of the principles of the disclosure, reference will now be made to the features illustrated in the drawings and specific language will be used to describe the same. It will nevertheless be understood that no limitation of the scope of the disclosure is thereby intended. Any alterations and further modifications, and any further applications of the principles of the disclosure as described herein are contemplated as would normally occur to one skilled in the art to which the disclosure relates. It will be apparent to those skilled in the relevant art that some features that are not relevant to the present disclosure may not be shown in the drawings for the sake of clarity.

As referenced in this application, the terms "stream," "gas stream," "vapor stream," and "liquid stream" refer to different stages of a feed stream as the feed stream is processed in a distillation tower that separates methane, the primary hydrocarbon in natural gas, from contaminants. Although the phrases "gas stream," "vapor stream," and "liquid stream," refer to situations where a gas, vapor, and liquid is mainly present in the stream, respectively, there may be other phases also present within the stream. For example, a gas may also be present in a "liquid stream." In some instances, the terms "gas stream" and "vapor stream" may be used interchangeably.

The disclosure relates to a system and method for separating a feed stream in a distillation tower. The system and method may destabilize solids that may adhere and/or accumulate in the controlled freeze zone section. The system and method may prevent solids that may adhere and accumulate in the controlled freeze zone section from adhering and/or accumulating. FIGS. 1-8 of the disclosure display various aspects of the system and method.

The system and method may separate a feed stream having methane and contaminants. The system may comprise a distillation tower 104, 204 (FIGS. 1-4). The distillation tower 104, 204 may separate the contaminants from the methane.

The distillation tower 104, 204 may be separated into three functional sections: a lower section 106, a middle controlled freeze zone section 108 and an upper section 110. The distillation tower 104, 204 may incorporate three functional sections when the upper section 110 is needed and/or desired. The distillation tower 104, 204 may incorporate only two functional sections when the upper section 110 is not needed and/or desired. When the distillation tower does not include an upper section 110, a portion of vapor leaving the middle controlled freeze zone section 108 may be extracted from the distillation tower 104, 204 as line 21 for disposing the vapors off the middle controlled freeze zone section while they are off specification with too high a contaminant content or for use as fuel or for other purposes, with the remaining vapor not extracted in line 14. Note that line 23 and line 14 are directly connected in FIGS. 2 and 4 in this instance. Line 14 enters the condenser 122 where a portion of the vapor may be condensed and returned as a liquid spray stream via a spray assembly 129. Moreover, lines 18 and 20 in FIGS. 1 and 3 or line 18 in FIGS. 2 and 4 may be eliminated, elements 124 and 126 in FIGS. 1 and 3 may be one and the same, and elements 150 and 128 in FIGS. 1 and 3 may be one and the same. The stream in line 14 in FIGS. 1 and 3, now taking the vapors leaving the middle controlled freeze section 108, directs these vapors to the condenser 122.

The lower section 106 may also be referred to as a stripper section. The middle controlled freeze zone section 108 may also be referred to as a controlled freeze zone section. The upper section 110 may also be referred to as a rectifier section.

Figure 3:
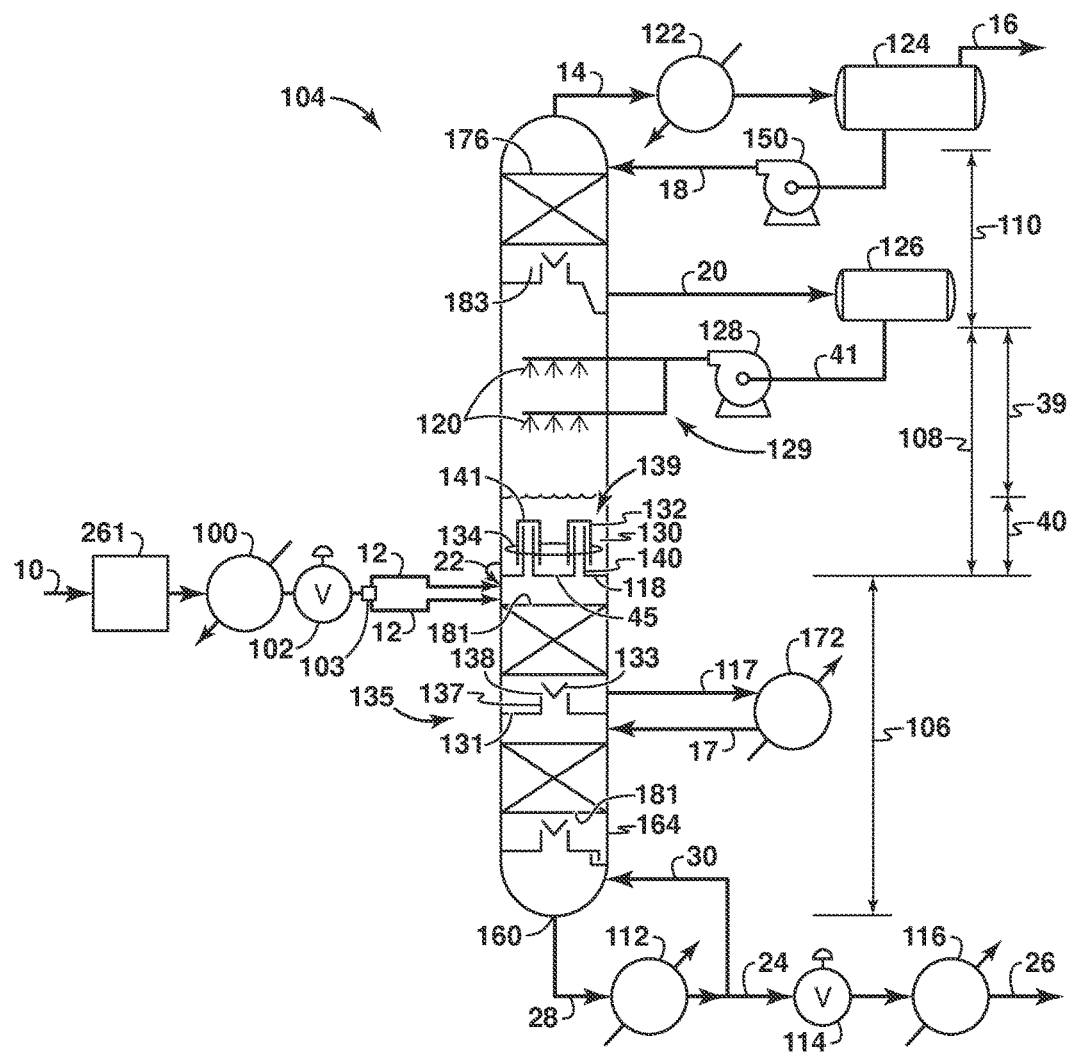
FIG. 3 is a schematic diagram of a tower with sections within a single vessel.

The sections of the distillation tower 104 may be housed within a single vessel (FIGS. 1 and 3). For example, the lower section 106, the middle controlled freeze zone section 108, and the upper section 110 may be housed within a single vessel 164.

Figure 2:
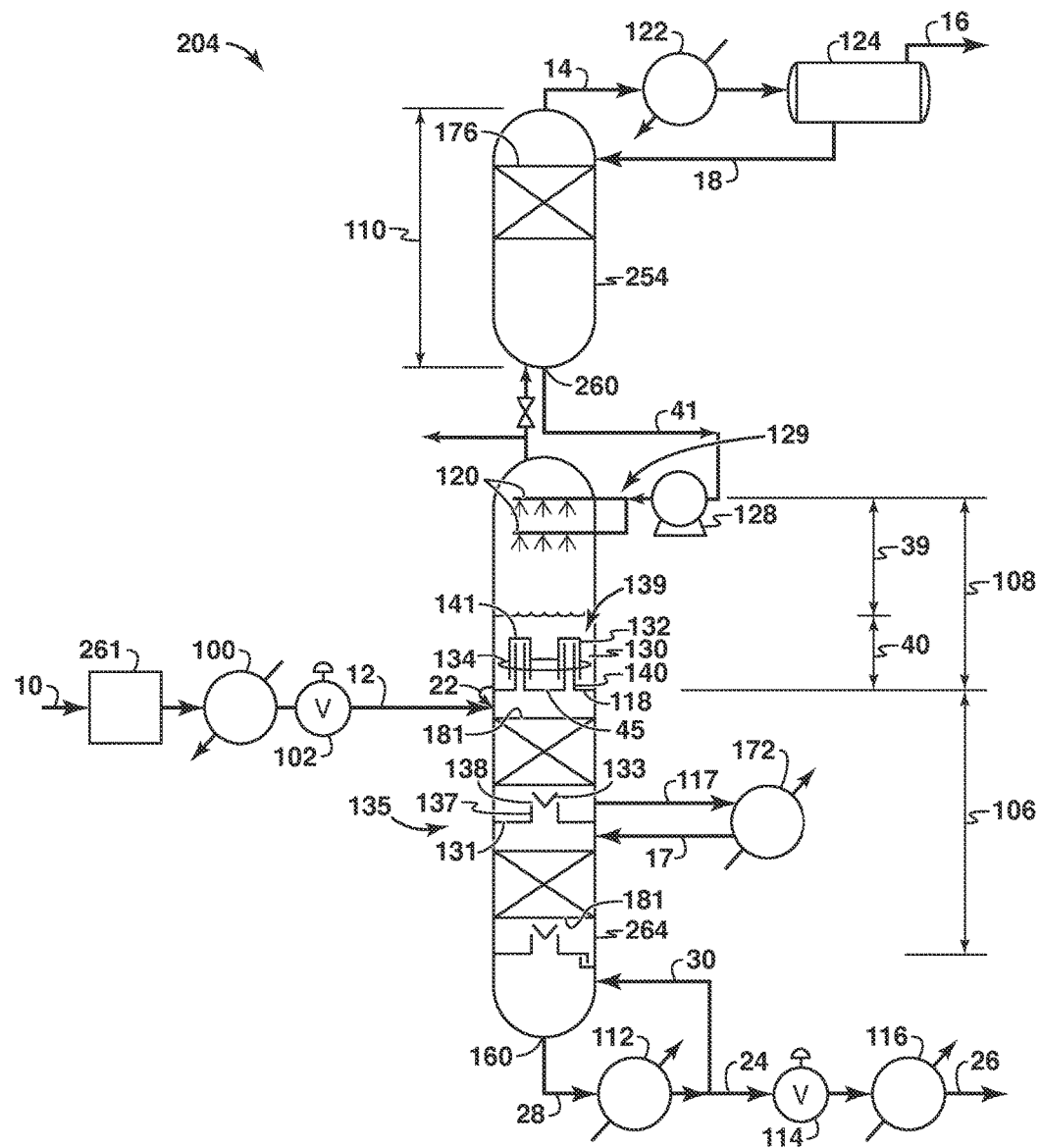
FIG. 2 is a schematic diagram of a tower with sections within multiple vessels.
Figure 4:
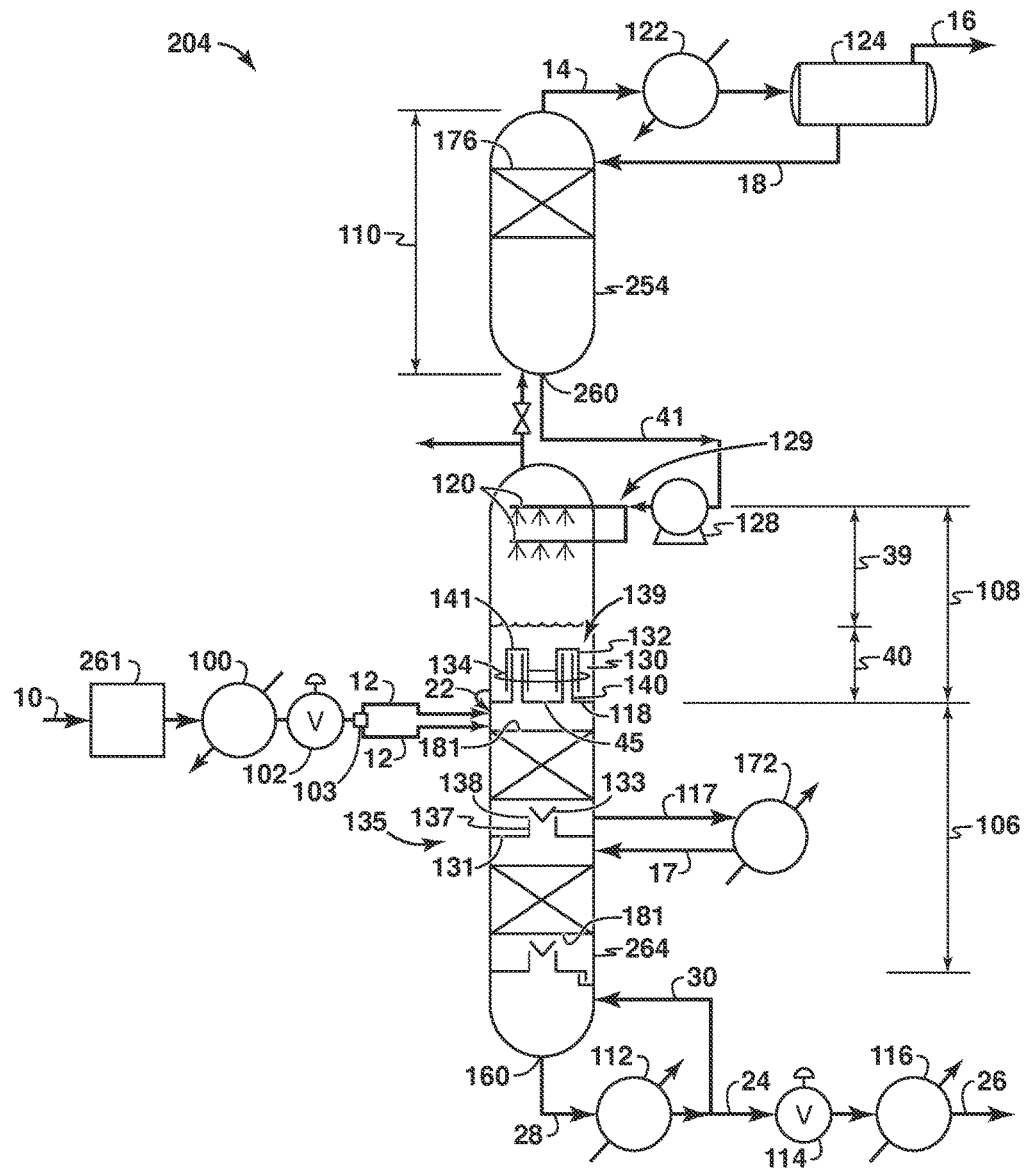
FIG. 4 is a schematic diagram of a tower with sections within multiple vessels.

The sections of the distillation tower 204 may be housed within a plurality of vessels to form a split-tower configuration (FIGS. 2 and 4). Each of the vessels may be separate from the other vessels. Piping and/or another suitable mechanism may connect one vessel to another vessel. In this instance, the lower section 106, middle controlled freeze zone section 108 and upper section 110 may be housed within two or more vessels. For example, as shown in FIGS. 2 and 4, the upper section 110 may be housed within a single vessel 254 and the lower and middle controlled freeze zone sections 106, 108 may be housed within a single vessel 264. When this is the case, a liquid stream exiting the upper section 110, may exit through a liquid outlet bottom 260. The liquid outlet bottom 260 is at the bottom of the upper section 110. Although not shown, each of the sections may be housed within its own separate vessel, or one or more section may be housed within separate vessels, or the upper and middle controlled freeze zone sections may be housed within a single vessel and the lower section may be housed within a single vessel, etc. When sections of the distillation tower are housed within vessels, the vessels may be side-by-side along a horizontal line and/or above each other along a vertical line.

The split-tower configuration may be beneficial in situations where the height of the distillation tower, motion considerations, and/or transportation issues, such as for remote locations, need to be considered. This split-tower configuration allows for the independent operation of one or more sections. For example, when the upper section is housed within a single vessel and the lower and middle controlled freeze zone sections are housed within a single vessel, independent generation of reflux liquids using a substantially contaminant-free, largely hydrocarbon stream from a packed gas pipeline or an adjacent hydrocarbon line, may occur in the upper section. And the reflux may be used to cool the upper section, establish an appropriate temperature profile in the upper section, and/or build up liquid inventory at the bottom of the upper section to serve as an initial source of spray liquids for the middle controlled freeze zone section. Moreover, the middle controlled freeze zone and lower sections may be independently prepared by chilling the feed stream, feeding it to the optimal location be that in the lower section or in the middle controlled freeze zone section, generating liquids for the lower and the middle controlled freeze zone sections, and disposing the vapors off the middle controlled freeze zone section while they are off specification with too high a contaminant content. Also, liquid from the upper section may be intermittently or continuously sprayed, building up liquid level in the bottom of the middle controlled freeze zone section and bringing the contaminant content in the middle controlled freeze zone section down and near steady state level so that the two vessels may be connected to send the vapor stream from the middle controlled freeze zone section to the upper section, continuously spraying liquid from the bottom of the upper section into the middle controlled freeze zone section and stabilizing operations into steady state conditions. The split tower configuration may utilize a sump of the upper section as a liquid receiver for the pump 128, therefore obviating the need for a liquid receiver 126 in FIGS. 1 and 3.

The system may also include a heat exchanger 100 (FIGS. 1-4). The feed stream 10 may enter the heat exchanger 100 before entering the distillation tower 104, 204. The feed stream 10 may be cooled within the heat exchanger 100. The heat exchanger 100 helps drop the temperature of the feed stream 10 to a level suitable for introduction into the distillation tower 104, 204.

The system may include an expander device 102 (FIGS. 1-4). The feed stream 10 may enter the expander device 102 before entering the distillation tower 104, 204. The feed stream 10 may be expanded in the expander device 102 after exiting the heat exchanger 100. The expander device 102 helps drop the temperature of the feed stream 10 to a level suitable for introduction into the distillation tower 104, 204. The expander device 102 may be any suitable device, such as a valve. If the expander device 102 is a valve, the valve may be any suitable valve that may aid in cooling the feed stream 10 before it enters the distillation tower 104, 204. For example, the expander device 102 may comprise a Joule-Thompson (J-T) valve.

The system may include a feed separator 103 (FIGS. 3-4). The feed stream may enter the feed separator before entering the distillation tower 104, 204. The feed separator may separate a feed stream having a mixed liquid and vapor stream into a liquid stream and a vapor stream. Lines 12 may extend from the feed separator to the distillation tower 104, 204. One of the lines 12 may receive the vapor stream from the feed separator. Another one of the lines 12 may receive the liquid stream from the feed separator. Each of the lines 12 may extend to the same and/or different sections (i.e.

middle controlled freeze zone, and lower sections) of the distillation tower 104, 204. The expander device 102 may or may not be downstream of the feed separator 103. The expander device 102 may comprise a plurality of expander devices 102 such that each line 12 has an expander device 102.

The system may include a dehydration unit 261 (FIGS. 1-4). The feed stream 10 may enter the dehydration unit 261 before entering the distillation tower 104, 204. The feed stream 10 enters the dehydration unit 261 before entering the heat exchanger 100 and/or the expander device 102. The dehydration unit 261 removes water from the feed stream 10 to prevent water from later presenting a problem in the heat exchanger 100, expander device 102, feed separator 103, or distillation tower 104, 204. The water can present a problem by forming a separate water phase (i.e., ice and/or hydrate) that plugs lines, equipment or negatively affects the distillation process. The dehydration unit 261 dehydrates the feed stream to a dew point sufficiently low to ensure a separate water phase does not form at any point downstream during the rest of the process. The dehydration unit may be any suitable dehydration mechanism, such as a molecular sieve or a glycol dehydration unit.

The system may include a filtering unit (not shown). The feed stream 10 may enter the filtering unit before entering the distillation tower 104, 204. The filtering unit may remove undesirable contaminants from the feed stream before the feed stream enters the distillation tower 104, 204. Depending on what contaminants are to be removed, the filtering unit may be before or after the dehydration unit 261 and/or before or after the heat exchanger 100.

The system may include a line 12 (FIGS. 1-4). The line may also be referred to as an inlet channel 12. The feed stream 10 may be introduced into the distillation tower 104, 204 through the line 12. The line 12 may extend to the lower section 106 or the middle controlled freeze zone section 108 of the distillation tower 104, 204. For example, the line 12 may extend to the lower section 106 such that the feed stream 10 may enter the lower section 106 of the distillation tower 104, 204 (FIGS. 1-4). The line 12 may directly or indirectly extend to the lower section 106 or the middle controlled freeze zone section 108. The line 12 may extend to an outer surface of the distillation tower 104, 204 before entering the distillation tower.

The lower section 106 is constructed and arranged to separate the feed stream 10 into an enriched contaminant bottom liquid stream (i.e., liquid stream) and a freezing zone vapor stream (i.e., vapor stream). The lower section 106 separates the feed stream at a temperature and pressure at which no solids form. The liquid stream may comprise a greater quantity of contaminants than of methane. The vapor stream may comprise a greater quantity of methane than of contaminants. In any case, the vapor stream is lighter than the liquid stream. As a result, the vapor stream rises from the lower section 106 and the liquid stream falls to the bottom of the lower section 106.

The lower section 106 may include and/or connect to equipment that separates the feed stream. The equipment may comprise any suitable equipment for separating methane from contaminants, such as one or more packed sections 181, or one or more distillation trays with perforations, downcomers, and weirs (FIGS. 1-4).

The equipment may include components that apply heat to the stream to form the vapor stream and the liquid stream. For example, the equipment may comprise a first reboiler 112 that applies heat to the stream. The first reboiler 112 may be located outside of the distillation tower 104, 204. The equipment may also comprise a second reboiler 172 that applies heat to the stream. The second reboiler 172 may be located outside of the distillation tower 104, 204. Line 117 may lead from the distillation tower to the second reboiler 172. Line 17 may lead from the second reboiler 172 to the distillation tower. Additional reboilers, set up similarly to the second reboiler described above, may also be used.

The first reboiler 112 may apply heat to the liquid stream that exits the lower section 106 through a liquid outlet 160 of the lower section 106. The liquid stream may travel from the liquid outlet 160 through line 28 to reach the first reboiler 112 (FIGS. 1-4). The amount of heat applied to the liquid stream by the first reboiler 112 can be increased to separate more methane from contaminants. The more heat applied by the first reboiler 112 to the stream, the more methane separated from the liquid contaminants, though more contaminants will also be vaporized.

The first reboiler 112 may also apply heat to the stream within the distillation tower 104, 204. Specifically, the heat applied by the first reboiler 112 warms up the lower section 106. This heat travels up the lower section 106 and supplies heat to warm solids entering a melt tray assembly 139 (FIGS. 1-4) of the middle controlled freeze zone section 108 so that the solids form a liquid and/or slurry mix.

The second reboiler 172 applies heat to the stream within the lower section 106. This heat is applied closer to the middle controlled freeze zone section 108 than the heat applied by the first reboiler 112. As a result, the heat applied by the second reboiler 172 reaches the middle controlled freeze zone section 108 faster than the heat applied by the first reboiler 112. The second reboiler 172 also helps with energy integration.

The equipment may include a chimney assembly 135 (FIGS. 1-4). While falling to the bottom of the lower section 106, the liquid stream may encounter one or more of the chimney assemblies 135.

Each chimney assembly 135 includes a chimney tray 131 that collects the liquid stream within the lower section 106. The liquid stream that collects on the chimney tray 131 may be fed to the second reboiler 172. After the liquid stream is heated in the second reboiler 172, the stream may return to the middle controlled freeze zone section 106 to supply heat to the middle controlled freeze zone section 106 and/or the melt tray assembly 139. Unvaporized stream exiting the second reboiler 172 may be fed back to the distillation tower 104, 204 below the chimney tray 131. Vapor stream exiting the second reboiler 172 may be routed under or above the chimney tray 131 when the vapor stream enters the distillation tower 104, 204.

The chimney tray 131 may include one or more chimneys 137. The chimney 137 serves as a channel that the vapor stream in the lower section 106 traverses. The vapor stream travels through an opening in the chimney tray 131 at the bottom of the chimney 137 to the top of the chimney 137. The opening is closer to the bottom of the lower section 106 than it is to the bottom of the middle controlled freeze zone section 108. The top is closer to the bottom of the middle controlled freeze zone section 108 than it is to the bottom of the lower section 106.

Each chimney 137 has attached to it a chimney cap 133. The chimney cap 133 covers a chimney top opening 138 of the chimney 137. The chimney cap 133 prevents the liquid stream from entering the chimney 137. The vapor stream exits the chimney assembly 135 via the chimney top opening 138.

After falling to the bottom of the lower section 106, the liquid stream exits the distillation tower 104, 204 through the liquid outlet 160. The liquid outlet 160 is within the lower section 106 (FIGS. 1-4). The liquid outlet 160 may be located at the bottom of the lower section 106.

After exiting through the liquid outlet 160, the feed stream may travel via line 28 to the first reboiler 112. The feed stream may be heated by the first reboiler 112 and vapor may then re-enter the lower section 106 through line 30. Unvaporized liquid may continue out of the distillation process via line 24.

The system may include an expander device 114 (FIGS. 1-4). After entering line 24, the heated liquid stream may be expanded in the expander device 114. The expander device 114 may be any suitable device, such as a valve. The valve 114 may be any suitable valve, such as a J-T valve.

The system may include a heat exchanger 116 (FIGS. 1-4). The liquid stream heated by the first reboiler 112 may be cooled or heated by the heat exchanger 116. The heat exchanger 116 may be a direct heat exchanger or an indirect heat exchanger. The heat exchanger 116 may comprise any suitable heat exchanger.

The vapor stream in the lower section 106 rises from the lower section 106 to the middle controlled freeze zone section 108. The middle controlled freeze zone section 108 is constructed and arranged to separate the feed stream 10 introduced into the middle controlled freeze zone section, or into the top of lower section 106, into a solid and a vapor stream. The solid may be comprised more of contaminants than of methane. The vapor stream (i.e., methane-enriched vapor stream) may comprise more methane than contaminants.

Figure 5:
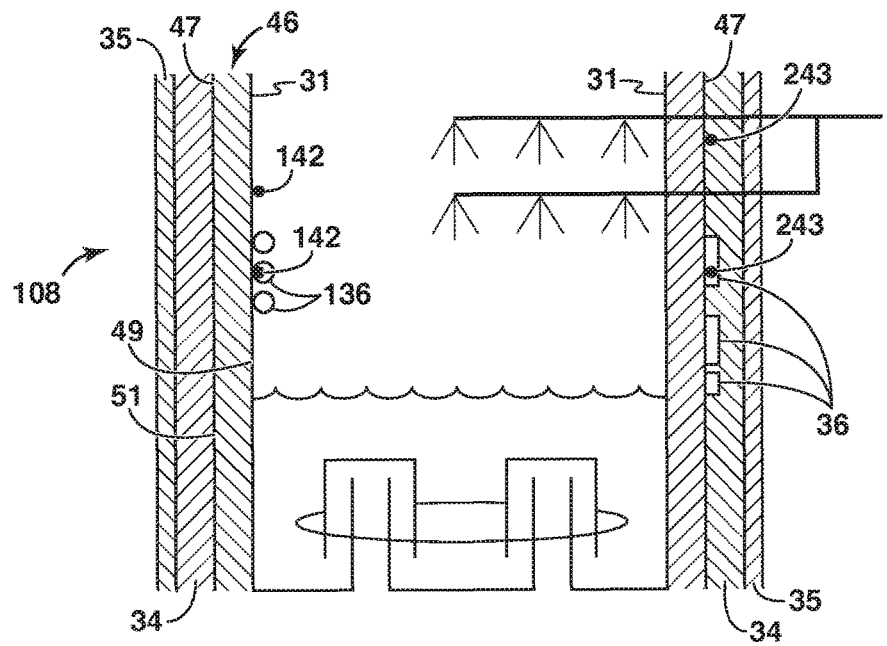
FIG. 5 is a schematic, cross-sectional diagram of the controlled freeze zone section of a distillation tower.

The middle controlled freeze zone section 108 includes a lower section 40 and an upper section 39 (FIG. 5). The lower section 40 is below the upper section 39. The lower section 40 directly abuts the upper section 39. The lower section 40 is primarily but not exclusively a heating section of the middle controlled freeze zone section 108. The upper section 39 is primarily but not exclusively a cooling section of the middle controlled freeze zone section 108. The temperature and pressure of the upper section 39 are chosen so that the solid can form in the middle controlled freeze zone section 108.

The middle controlled freeze zone section 108 may comprise a melt tray assembly 139 that is maintained in the middle controlled freeze zone section 108 (FIGS. 1-4). The melt tray assembly 139 is within the lower section 40 of the middle controlled freeze zone section 108. The melt tray assembly 139 is not within the upper section 39 of the middle controlled freeze zone section 108.

The melt tray assembly 139 is constructed and arranged to melt a solid formed in the middle controlled freeze zone section 108. When the warm vapor stream rises from the lower section 106 to the middle controlled freeze zone section 108, the vapor stream immediately encounters the melt tray assembly 139 and supplies heat to melt the solids. The melt tray assembly 139 may comprise at least one of a melt tray 118, a bubble cap 132, a liquid 130 and heat mechanism(s) 134.

The melt tray 118 may collect a liquid and/or slurry mix. The melt tray 118 divides at least a portion of the middle controlled freeze zone section 108 from the lower section 106. The melt tray 118 is at the bottom 45 of the middle controlled freeze zone section 108.

One or more bubble caps 132 may act as a channel for the vapor stream rising from the lower section 106 to the middle controlled freeze zone section 108. The bubble cap 132 may provide a path for the vapor stream up the riser 140 and then down and around the riser 140 to the melt tray 118. The riser 140 is covered by a cap 141. The cap 141 prevents the liquid 130 from travelling into the riser and it also helps prevent solids from travelling into the riser 140. The vapor stream's traversal through the bubble cap 132 allows the vapor stream to transfer heat to the liquid 130 within the melt tray assembly 139.

One or more heat mechanisms 134 may further heat up the liquid 130 to facilitate melting of the solids into a liquid and/or slurry mix. The heat mechanism(s) 134 may be located anywhere within the melt tray assembly 139. For example, as shown in FIGS. 1-4, a heat mechanism 134 may be located around bubble caps 132. The heat mechanism 134 may be any suitable mechanism, such as a heat coil. The heat source of the heat mechanism 134 may be any suitable heat source.

The liquid 130 in the melt tray assembly 139 is heated by the vapor stream. The liquid 130 may also be heated by the one or more heat mechanisms 134. The liquid 130 helps melt the solids formed in the middle controlled freeze zone section 108 into a liquid and/or slurry mix. Specifically, the heat transferred by the vapor stream heats up the liquid, thereby enabling the heat to melt the solids. The liquid 130 is at a level sufficient to melt the solids.

While in the liquid 130, hydrocarbons may be separated from the contaminants. The hydrocarbons separated from the contaminants may form part of the vapor stream (i.e., the hydrocarbon-enriched vapor stream), and may rise from the lower section 40 to the upper section 39 of the middle controlled freeze zone section 108.

The middle controlled freeze zone section 108 may include a heating mechanism 36, 136. The heating mechanism 36, 136 may be coupled to at least one of a controlled freeze zone internal surface 31 (FIG. 5) of a controlled freeze zone wall 46 (FIG. 5) and a controlled freeze zone external surface 47 (FIGS. 5-7) of the controlled freeze zone wall 46.

The controlled freeze zone internal surface 31 is the inside surface of the middle controlled freeze zone section 108 (FIG. 5). The controlled freeze zone internal surface 31 may not be the innermost inside surface of the middle controlled freeze zone section 108 when the heating mechanism is coupled to the controlled freeze zone internal surface 31. The heating mechanism may be the innermost inside surface of the middle controlled freeze zone section 108.

The controlled freeze zone external surface 47 is the outside surface of the middle controlled freeze zone section 108 (FIG. 5). The controlled freeze zone external surface 47 may not be the outermost surface of the middle controlled freeze zone section 108.

Insulation 34 and its cladding 35 may be on top of the controlled freeze zone external surface 47 (FIG. 5). The insulation 34 and its cladding 35 may be the outermost surface of the middle controlled freeze zone section 108. The insulation 34 may be on top of the controlled freeze zone external surface 47 such that the controlled freeze zone external surface 47 may be on an outer surface of the middle controlled freeze zone section 108.

The heating mechanism 36, 136 may be controlled in a manner to provide optimal amount of heat to destabilize and/or prevent adhesion of solids in the middle controlled freeze zone section 108. The heating mechanism 36, 136 may be controlled in a manner to prevent any adverse effects from excessive heat input into the middle controlled freeze zone section 108. In essence, the coupling is controlled such that heat emitted by the heating mechanism 36, 136 is localized to the controlled freeze zone wall 46 where solids adhere.

To provide an optimal amount of heat, the heating mechanism 36, 136 may be controlled by a temperature controller or by an electrical power controller. The temperature controller controls the temperature of the heating mechanism 36, 136. The electrical power controller controls the electrical power of the heating mechanism 36, 136.

The heating mechanism 36, 136 may be above and/or below the uppermost portion of the melt tray assembly 139 of the middle controlled freeze zone section 108. The heating mechanism 36, 136 may be in the uppermost section 39 of the middle controlled freeze zone section 108.

Figure 6:
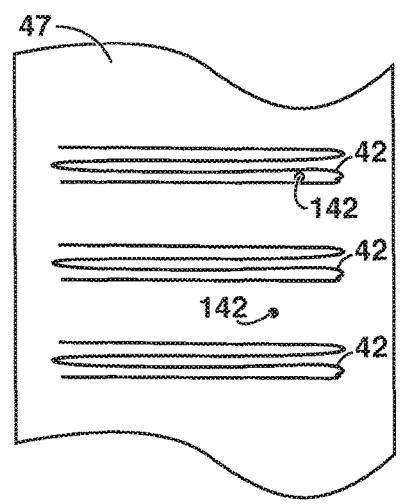
FIG. 6 is a schematic diagram of section 38 of FIG. 5 when the heating mechanism comprises a heating coil.
Figure 7:
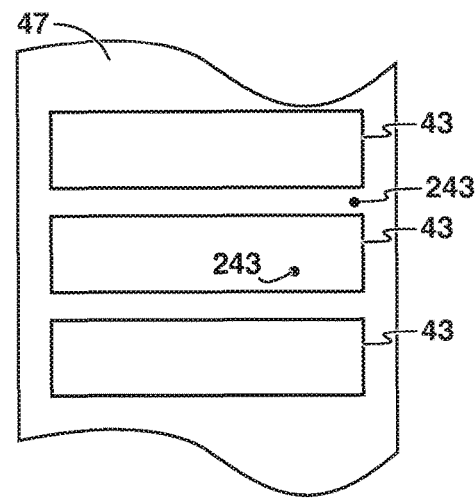
FIG. 7 is a schematic diagram of section 38 of FIG. 5 when the heating mechanism comprises an electrical conductor.

The heating mechanism 36, 136 may comprise one or more heating mechanisms 36, 136. For example, as shown in FIGS. 5-7, the heating mechanism 36, 136 may comprise three heating mechanisms. Each of the heating mechanisms 36, 136 may be directly adjacent to another of the heating mechanisms. One or more of the heating mechanisms 36, 136 may be within a heating zone of the middle controlled freeze zone section 108. Each of the heating mechanisms 36, 136 within the heating zone is responsible for heating the portion of the controlled freeze zone wall 46 within the heating zone. There may be a plurality of heating zones.

When the heating mechanism 36, 136 comprises multiple heating mechanisms, one or more of the heating mechanisms may or may not be connected together. When heating mechanisms are connected, the heating mechanisms may be operated together. When heating mechanisms are not connected, the heating mechanisms may be operated independently. The independent operation of heating mechanisms may allow for optimal heating control of one or more heating zones of the middle controlled freeze zone section 108. The independent operation of heating mechanisms may allow less total heating of the middle controlled freeze zone section 108, thereby improving the efficiency of the distillation tower 104, 204. When the heating mechanisms are connected, the heating mechanisms may be operated dependently. The dependent operation of the heating mechanisms may allow for the heating mechanisms to be operated more simplistically than independent operation of the heating mechanism.

The amount and/or size of heating mechanisms 36, 136 in the middle controlled freeze zone section 108 may depend on a variety of factors. The factors may include the size of the distillation tower 104, 204, the thickness of the controlled freeze zone wall 46, the temperature of the liquid spray stream being sprayed from the spray assembly 129, the flow rate of the feed stream 10, and/or the temperature outside of the distillation tower 104, 204. The more feed stream 10 that enters the distillation tower 104, 204, the more liquid spray stream sprayed. The thicker the controlled freeze zone wall 46 and/or lower the temperature outside of the distillation tower 104, 204, the more heat the heating mechanism 36, 136 may need to produce.

The heating mechanism 36, 136 destabilizes and/or prevents adhesion of the solids to the controlled freeze zone wall 46. When fully heated, the temperature of the heating mechanism 36, 136 is above the solidification temperature of the solid. Consequently, the ability of the solid to accumulate and/or adhere to the controlled freeze zone wall 46 is reduced because the adhesion of the solids to the controlled freeze zone wall 46 is prevented and/or adhered solids are destabilized by the heating mechanism 36, 136. To the extent that any solid has adhered to the controlled freeze zone wall 46, such as before the heating mechanism 36, 136 is turned on or has heated up to be a temperature above the solidification temperature of the solid, or because of an operational upset, the heating mechanism 36, 136 causes the solid to detach from the controlled freeze zone wall 46 after the heating mechanism 36, 136 is at a temperature above the solidification temperature of the solid.

The heating mechanism 36, 136 may completely extend around at least one of an internal circumference 49 of the controlled freeze zone internal surface 31 and an external circumference 51 of the controlled freeze zone external surface 47. Alternatively, the heating mechanism 36, 136 may extend around a portion of at least one of the internal circumference 49 and the external circumference 51. The amount of the internal or external circumference that the heating mechanism 36, 136 extends around depends on the amount of the controlled freeze zone wall 46 heated by the heating mechanism 36, 136.

The heating mechanism 36, 136 may be any suitable heating mechanism 36, 136. For example, the heating mechanism 36, 136 may be one of a coil 42 (FIG. 6) and an electrical conductor 43 (FIG. 7). When the heating mechanism 36, 136 is coupled to the controlled freeze zone internal surface 31, the heating mechanism 36, 136 may be any source of heat that can be safely deployed inside a distillation tower without, for example, being a potential source of combustion.

When the heating mechanism 36, 136 is a coil, the coil 42 may receive a fluid at a temperature above the solidification temperature of the solid. The fluid within the coil 42 transfers heat to at least one of the controlled freeze zone wall 46, the inside of the upper section 39 of the middle controlled freeze zone section 108, and the liquid on the melt tray 118. The transferred heat destabilizes and/or prevents the adhesion of the solid to the controlled freeze zone wall 46. The fluid within the coil 42 directly transfers heat to the controlled freeze zone wall 46 when the coil 42 is coupled to the controlled freeze zone external surface 47 or the controlled freeze zone internal surface 31. When the heating mechanism 36, 136 is coupled to the controlled freeze zone internal surface 31, the heating mechanism 36, 136 is a coil 42 to avoid the potential of a fire occurring inside the distillation tower 104, 204. The fluid within the coil may be any suitable fluid. For example, the fluid may be any fluid whose inlet temperature and/or flow rate can be controlled, and whose freezing point is substantially lower than that of the freezing $CO_2$. Examples of fluid include, but are not limited to, propane, methanol, and/or other commercially-available low-melting temperature heat transfer fluids.

When the heating mechanism 36, 136 is an electrical conductor 43, the electrical conductor operates at a temperature above the solidification temperature of the solid. The electrical conductor 43 may be any suitable electrical conductor 43. For example, the electrical conductor 43 may comprise aluminum solid alloy or copper. The heating mechanism 36, 136 may be an electrical conductor 43 when the heating mechanism 36, 136 is coupled to the controlled freeze zone external surface 47 and not the controlled freeze zone internal surface 31 to avoid the potential of a fire occurring inside the distillation tower.

A certain amount of heat may be applied by the heating mechanism 36, 136 to ensure destabilization of solids and/or to prevent adhesion of solids within the middle controlled freeze zone section 108. The certain amount of heat is enough heat to bring an internal surface of the middle controlled freeze zone section 108 to a temperature slightly above the freezing point of $CO_2$. The certain amount of heat is not excessive so as to not to impact negatively the normal operation of the middle controlled freeze zone section 108.

Previous technology did not supply heat by a heating mechanism 36, 136 within a middle controlled freeze zone section 108 because it was not expected that solids would adhere to the middle controlled freeze zone section. Instead it was expected that solids would fall to the melt tray assembly 139 without adhering to the middle controlled freeze zone section. It was also not expected that the elements within the middle controlled freeze zone section would interfere with the pathway of the solids such that the solids would adhere to the middle controlled freeze zone section instead of falling to the melt tray assembly 139.

A temperature of the heating mechanism 36, 136 and/or the controlled freeze zone wall 46 may be detected with a temperature sensor 142, 243 (FIGS. 6-7). When the middle controlled freeze zone section 108 includes multiple heating mechanisms 36, 136, the temperature of one or more of the heating mechanism 36, 136 may be detected with the temperature sensors.

The middle controlled freeze zone section 108 may include the temperature sensor 142, 243. The temperature sensor 142, 243 may be on any surface of the middle controlled freeze zone section 108. For example, the temperature sensor may be at least one of coupled to the controlled freeze zone internal surface 31 (FIG. 5), the controlled freeze zone external surface 47 and the insulation 34. Surfaces of the middle controlled freeze zone section 108 include the controlled freeze zone internal surface 31, the controlled freeze zone external surface 47, the insulation 34, surfaces of the spray assembly 129, surfaces of the melt tray assembly 139, etc. The temperature sensor 142, 243 may be within at least one of the lower section 40 and the upper section 39 of the middle controlled freeze zone section 108. Temperature sensors may be spaced at intervals throughout the middle controlled freeze zone section 108.

The temperature sensor 142, 243 detects temperature at and/or around the area surrounding the temperature sensor 142, 243. A baseline temperature for each temperature sensor 142, 243 is determined while the middle controlled freeze zone section 108 is properly functioning. A temperature deviation outside of an expected temperature range of the temperature detected by the temperature sensor 142, 243 (i.e., the detected temperature) from the baseline temperature may indicate that the middle controlled freeze zone section 108 is not properly functioning. The temperature deviation may be about 2 to 10 degrees C. or 2 to 10 degrees C.

The middle controlled freeze zone section 108 may be deemed to be not properly functioning if one or more of a variety of circumstances occur. The variety of circumstances may include if solids build-up on the controlled freeze zone wall 46, if the middle controlled freeze zone section 108 is too warm to form solids, if the middle controlled freeze zone section 108 is too cold to melt the solids in the melt tray assembly 139, etc. For example, if the temperature sensor 142, 243 is coupled to the controlled freeze zone external surface 47 within the upper section 39 of the middle controlled freeze zone section 108 then the temperature sensor 142, 243 is expected to detect a fairly cold temperature that is close to the actual temperature of the liquid spray stream within the middle controlled freeze zone section 108. If the temperature sensor 142, 243 detects a rise in temperature from that expected of the actual temperature of the liquid spray stream, then the rise in temperature may indicate that solids have built-up on the controlled freeze zone wall 46. The solid acts as an insulator so solid build-up on the controlled freeze zone wall 46 is determined when there is an unexpected rise in temperature read by the temperature sensor 142, 243.

As it relates to the heating mechanism, the detected temperature helps determine whether the heating mechanism 36, 136 is working in a manner to destabilize and/or prevent adhesion of solid on the controlled freeze zone wall 46. If the temperature detected by the temperature sensor 142, 243 falls outside of the expected temperature range, the temperature sensor 142, 243 may indicate that the heating mechanism 36, 136 is not working in a manner to destabilize and/or prevent adhesion of solid on the controlled freeze zone wall 46. In this instance, the heating mechanism 36, 136 may be manipulated to apply more heat to the controlled freeze zone wall 46. In addition or alternatively, measures may be taken to destabilize and/or prevent adhesion of the solid to the controlled freeze zone wall 46. The measures may include at least one of (a) applying a treatment mechanism and (b) using a modified spray assembly, such as those described in the applications entitled "Method and Device for Separating Hydrocarbons and Contaminants with a Surface Treatment Mechanism" (U.S. Ser. No. 61/912,987) and "Method and Device for Separating Hydrocarbons and Contaminants with a Spray Assembly," (U.S. Ser. No. 61/912,957) respectively, each by Jaime Valencia, et al. and filed on the same day as the instant application.

The temperature sensor 142, 243 may be any suitable temperature sensor. For example, the temperature sensor may comprise a thermocouple, platinum resistance thermometer, RTD and/or thermistor.

The temperature sensor 142, 243 may comprise a plurality of temperature sensors 142, 243. Each of the plurality of temperature sensors 142, 243 may be coupled to the same or different surface of the middle controlled freeze zone section 108. One or more of the temperature sensors 142, 243 may comprise an array of temperature sensors. One or more of the temperature sensors may be coupled to a surface of the middle controlled freeze zone section 108 at the same or different elevation of the middle controlled freeze zone section 108. While the temperature sensor 142, 243 is generally referred to as part of the middle controlled freeze zone section 108, a temperature sensor 142, 243 could be included in one or more of the lower section 106 and the upper section 110.

When the middle controlled freeze zone section 108 includes a heating mechanism 36, 136, the controlled freeze zone internal surface 31 may not have a treatment mechanism, such as the treatment mechanism described in the application entitled "Method and Device for Separating Hydrocarbons and Contaminants with a Surface Treatment Mechanism" (U.S. Ser. No. 61/912,987) by Jaime Valencia, et al and filed on the same day as the instant application. The middle controlled freeze zone section 108 including the heating mechanism 36, 136 may not use the treatment mechanism because the heating mechanism 36, 136 may adequately destabilize and/or prevent the adhesion of solids to the controlled freeze zone wall 46 without also being treated by the treatment mechanism. Alternatively, the middle controlled freeze zone section 108 including the heating mechanism 36, 136 may have the controlled freeze zone internal surface 31 treated with the treatment mechanism. Having the heating mechanism 36, 136 and controlled freeze zone internal surface 31 treated with the treatment mechanism may allow for a reduced energy input.

The middle controlled freeze zone section 108 may also comprise a spray assembly 129. The spray assembly 129 cools the vapor stream that rises from the lower section 40. The spray assembly 129 sprays liquid, which is cooler than the vapor stream, on the vapor stream to cool the vapor stream. The spray assembly 129 is within the upper section 39. The spray assembly 129 is not within the lower section 40. The spray assembly 129 is above the melt tray assembly 139. In other words, the melt tray assembly 139 is below the spray assembly 129.

The spray assembly 129 includes one or more spray nozzles 120 (FIGS. 1-4). Each spray nozzle 120 sprays liquid on the vapor stream. The spray assembly 129 may also include a spray pump 128 (FIGS. 1-4) that pumps the liquid. Instead of a spray pump 128, gravity may induce flow in the liquid.

Figure 8:
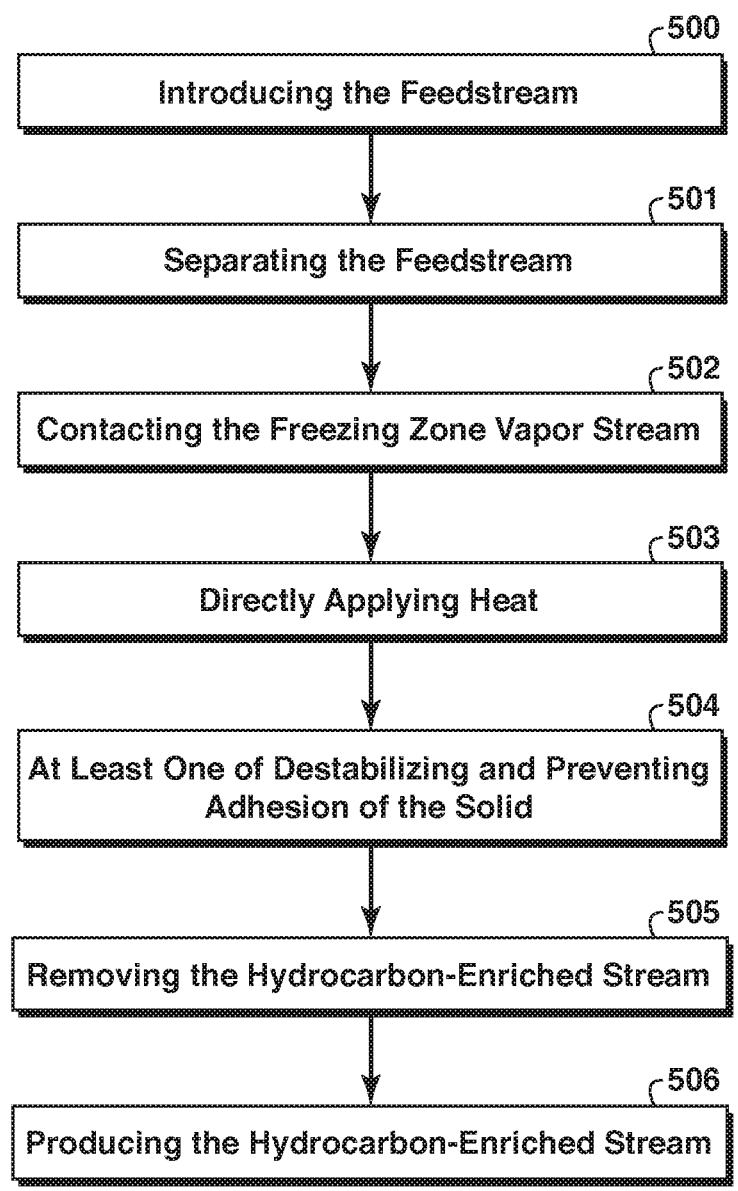
FIG. 8 is a flowchart of a method within the scope of the present disclosure.

The liquid sprayed by the spray assembly 129 contacts the vapor stream at a temperature and pressure at which solids form. Solids, containing mainly contaminants, form when the sprayed liquid contacts the vapor stream, 502 (FIG. 8). The solids fall toward the melt tray assembly 139.

The temperature in the middle controlled freeze zone section 108 cools down as the vapor stream travels from the bottom of the middle controlled freeze zone section 108 to the top of the middle controlled freeze zone section 108. The methane in the vapor stream rises from the middle controlled freeze zone section 108 to the upper section 110. Some contaminants may remain in the methane and also rise. The contaminants in the vapor stream tend to condense or solidify with the colder temperatures and fall to the bottom of the middle controlled freeze zone section 108.

The solids form the liquid and/or slurry mix when in the liquid 130. Some of the liquid and/or slurry mix flows from the middle controlled freeze zone section 108 to the lower section 106. This liquid and/or slurry mix flows from the bottom of the middle controlled freeze zone section 108 to the top of the lower section 106 via a line 22 (FIGS. 1-4). The line 22 may be an exterior line. The line 22 may extend from the distillation tower 104, 204. The line 22 may extend from the middle controlled freeze zone section 108. The line may extend to the lower section 106. The line 22 may extend from an outer surface of the distillation tower 104, 204.

The vapor stream that rises in the middle controlled freeze zone section 108 and does not form solids or otherwise fall to the bottom of the middle controlled freeze zone section 108, rises to the upper section 110. The upper section 110 operates at a temperature and pressure and contaminant concentration at which no solid forms. The upper section 110 is constructed and arranged to cool the vapor stream to separate the methane from the contaminants. Reflux in the upper section 110 cools the vapor stream. The reflux is introduced into the upper section 110 via line 18. Line 18 may extend to the upper section 110. Line 18 may extend from an outer surface of the distillation tower 104, 204.

After contacting the reflux in the upper section 110, the feed stream forms a vapor stream and a liquid stream. The vapor stream mainly comprises methane. The liquid stream comprises relatively more contaminants. The vapor stream rises in the upper section 110 and the liquid falls to a bottom of the upper section 110.

To facilitate separation of the methane from the contaminants when the stream contacts the reflux, the upper section 110 may include one or more mass transfer devices 176. Each mass transfer device 176 helps separate the methane from the contaminants. Each mass transfer device 176 may comprise any suitable separation device, such as a tray with perforations, or a section of random or structured packing to facilitate contact of the vapor and liquid phases.

After rising, the vapor stream may exit the distillation tower 104, 204 through line 14. The line 14 may emanate from an upper part of the upper section 110. The line 14 may extend from an outer surface of the upper section 110.

From line 14, the vapor stream may enter a condenser 122. The condenser 122 cools the vapor stream to form a cooled stream. The condenser 122 at least partially condenses the stream.

After exiting the condenser 122, the cooled stream may enter a separator 124. The separator 124 separates the vapor stream into liquid and vapor streams. The separator may be any suitable separator that can separate a stream into liquid and vapor streams, such as a reflux drum.

Once separated, the vapor stream may exit the separator 124 as sales product. The sales product may travel through line 16 for subsequent sale to a pipeline and/or condensation to be liquefied natural gas.

Once separated, the liquid stream may return to the upper section 110 through line 18 as the reflux. The reflux may travel to the upper section 110 via any suitable mechanism, such as a reflux pump 150 (FIGS. 1 and 3) or gravity (FIGS. 2 and 4).

The liquid stream (i.e., freezing zone liquid stream) that falls to the bottom of the upper section 110 collects at the bottom of the upper section 110. The liquid may collect on tray 183 (FIGS. 1 and 3) or at the bottommost portion of the upper section 110 (FIGS. 2 and 4). The collected liquid may exit the distillation tower 104, 204 through line 20 (FIGS. 1 and 3) or outlet 260 (FIGS. 2 and 4). The line 20 may emanate from the upper section 110. The line 20 may emanate from a bottom end of the upper section 110. The line 20 may extend from an outer surface of the upper section 110.

The line 20 and/or outlet 260 connect to a line 41. The line 41 leads to the spray assembly 129 in the middle controlled freeze zone section 108. The line 41 emanates from the holding vessel 126. The line 41 may extend to an outer surface of the middle controlled freeze zone section 110.

The line 20 and/or outlet 260 may directly or indirectly (FIGS. 1-4) connect to the line 41. When the line 20 and/or outlet 260 directly connect to the line 41, the liquid spray may be sent to the spray nozzle(s) 120 via any suitable mechanism, such as the spray pump 128 or gravity. When the line 20 and/or outlet 260 indirectly connect to the line 41, the lines 20, 41 and/or outlet 260 and line 41 may directly connect to a holding vessel 126 (FIGS. 1 and 3). The holding vessel 126 may house at least some of the liquid spray before it is sprayed by the nozzle(s). The liquid spray may be sent from the holding vessel 126 to the spray nozzle(s) 120 via any suitable mechanism, such as the spray pump 128 (FIGS. 1-4) or gravity. The holding vessel 126 may be needed when there is not a sufficient amount of liquid stream at the bottom of the upper section 110 to feed the spray nozzles 120.

Persons skilled in the technical field will readily recognize that in practical applications, the use of one or more heating mechanisms to destabilize and/or prevent the adhesion of solids to a surface may be used in other apparatuses and/or systems beside distillation towers. For example, one or more heating mechanisms may be used in a physical removal process.

As shown in FIG. 8, a method for separating a feed stream 10 in the distillation tower 104, 204 and/or producing hydrocarbons may include introducing 500 the feed stream 10 into a section 106, 108 of the distillation tower 104, 204. As previously discussed in the instant application, the feed stream 10 is introduced into one of the sections 106, 108 via line 12. The method may also include separating 501 the feed stream 10 in the lower section 106 into the enriched contaminant bottom liquid stream and the freezing zone vapor stream at a temperature and pressure at which no solid forms. The lower section 106 operates as previously discussed in the instant application. Additionally, the method may include contacting 502 the freezing zone vapor stream in the middle controlled freeze zone section 108 with the freezing zone liquid stream at a temperature and pressure at which the freezing zone vapor stream forms the solid and the hydrocarbon-enriched vapor stream. The middle controlled freeze zone section 108 operates as previously discussed in the instant application. Moreover, the method may include directly applying heat 503 to the controlled freeze zone wall 46 and destabilizing and/or preventing 504 adhesion of the solid to the controlled freeze zone wall 46 with the heating mechanism 36, 136. The heating mechanism 36, 136 operates as previously discussed in the instant application.

The method may also include detecting a temperature of at least one of the heating mechanism 36, 136 and the controlled freeze zone wall 46. The temperature may be detected using the temperature sensor 142, 243 previously described. Information detected by the temperature sensor 142, 243 may be used as previously described.

The method may include maintaining an upper section 110. The upper section 110 operates as previously discussed in the instant application. The method may also include separating the feed stream in the upper section 110 as previously discussed in the instant application.

The method may include stabilizing the distillation tower 104, 204 via a suitable operational action if large amounts of solid are destabilized and fall into the melt tray assembly 139. One example of a suitable operational action includes, but is not limited to, controlling the liquid level in the melt tray assembly 139. One example of controlling the liquid level in the melt tray assembly 139 is described in the application entitled "A Method and System of Maintaining a Liquid Level in a Distillation Tower" (U.S. Ser. No. 61/912,959) by Jaime Valencia and filed on the same day as the instant application.

It is important to note that the steps depicted in FIG. 8 are provided for illustrative purposes only and a particular step may not be required to perform the inventive methodology. The claims, and only the claims, define the inventive system and methodology.

Disclosed aspects may be used in hydrocarbon management activities. As used herein, "hydrocarbon management" or "managing hydrocarbons" includes hydrocarbon extraction, hydrocarbon production, hydrocarbon exploration, identifying potential hydrocarbon resources, identifying well locations, determining well injection and/or extraction rates, identifying reservoir connectivity, acquiring, disposing of and/or abandoning hydrocarbon resources, reviewing prior hydrocarbon management decisions, and any other hydrocarbon-related acts or activities. The term "hydrocarbon management" is also used for the injection or storage of hydrocarbons or $CO_2$, for example the sequestration of $CO_2$, such as reservoir evaluation, development planning, and reservoir management. The disclosed methodologies and techniques may be used in extracting hydrocarbons from a subsurface region and processing the hydrocarbons. Hydrocarbons and contaminants may be extracted from a reservoir and processed. The hydrocarbons and contaminants may be processed, for example, in the distillation tower previously described. After the hydrocarbons and contaminants are processed, the hydrocarbons may be extracted from the processor, such as the distillation tower, and produced. The contaminants may be discharged into the Earth, etc. For example, as shown in FIG. 8, the method for producing hydrocarbons may also include removing 505 the hydrocarbon-enriched vapor stream from the distillation tower; and producing 506 the hydrocarbon-enriched vapor stream extracted from the distillation tower. The initial hydrocarbon extraction from the reservoir may be accomplished by drilling a well using hydrocarbon drilling equipment. The equipment and techniques used to drill a well and/or extract these hydrocarbons are well known by those skilled in the relevant art. Other hydrocarbon extraction activities and, more generally, other hydrocarbon management activities, may be performed according to known principles.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numeral ranges provided. Accordingly, these terms should be interpreted as indicating that insubstantial or inconsequential modifications or alterations of the subject matter described are considered to be within the scope of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be understood that numerous changes, modifications, and alternatives to the preceding disclosure can be made without departing from the scope of the disclosure. The preceding description, therefore, is not meant to limit the scope of the disclosure. Rather, the scope of the disclosure is to be determined only by the appended claims and their equivalents. It is also contemplated that structures and features in the present examples can be altered, rearranged, substituted, deleted, duplicated, combined, or added to each other.

The articles "the", "a" and "an" are not necessarily limited to mean only one, but rather are inclusive and open ended so as to include, optionally, multiple such elements.

What is claimed is:

1. A method for separating a feed stream in a distillation tower comprising:
   providing a distillation tower comprising a stripper section and a controlled freeze zone section, wherein the controlled freeze zone section comprises a lower section and an upper section, and wherein the controlled freeze zone section comprises a melt tray assembly in the lower section of the controlled freeze zone section;
   introducing a feed stream into one of the stripper section and the controlled freeze zone section of the distillation tower, the feed stream comprising a hydrocarbon and a contaminant;
   separating the feed stream in the stripper section into an enriched contaminant bottom liquid stream, comprising the contaminant, and a freezing zone vapor stream, comprising the hydrocarbon, at a temperature and pressure at which no solid forms;
   contacting the freezing zone vapor stream in the controlled freeze zone section with a freezing zone liquid stream, comprising the hydrocarbon, at a temperature and pressure at which a solid, comprising the contaminant, and a hydrocarbon-enriched vapor stream, comprising the hydrocarbon, form;

directly applying heat to a controlled freeze zone vertical wall of the controlled freeze zone section with a heating mechanism coupled to at least one of a controlled freeze zone internal surface of the controlled freeze zone vertical wall and a controlled freeze zone external surface of the controlled freeze zone vertical wall, wherein the heating mechanism is coupled to the controlled freeze zone vertical wall above the melt tray assembly; and at least one of destabilizing and preventing adhesion of the solid to the controlled freeze zone vertical wall with the heating mechanism.

2. The method of claim 1, wherein applying heat includes heating separate sections of the controlled freeze zone vertical wall with the heating mechanism.

3. The method of claim 1, wherein applying heat includes heating the upper section of the controlled freeze zone section.

4. The method of claim 1, wherein the heating mechanism comprises one of (a) a coil containing a fluid and (b) an electrical conductor.

5. The method of claim 1, further comprising detecting a temperature of the heating mechanism with a temperature sensor that is adjacent to the heating mechanism and coupled to at least one of the controlled freeze zone internal surface and the controlled freeze zone external surface.

6. The method of claim 1, further comprising melting or vaporizing the solid in the upper section of the controlled freeze zone section.

7. The method of claim 6, wherein the lower section of the controlled freeze zone section directly abuts and is separate from the upper section of the controlled freeze zone section and wherein the upper section of the controlled freeze zone section directly abuts and is separate from the lower section of the controlled freeze zone section.

8. The method of claim 1, further comprising producing the freezing zone liquid stream in a rectifier section of the distillation tower at a temperature and pressure at which substantially no solid forms.

9. The method of claim 8, wherein the distillation tower further comprises a rectifier section, and wherein at least one of the stripping section, the controlled freeze zone section, and the rectifier section are in a first vessel and another of the at least one of the stripping section, the controlled freeze zone section, and the rectifier section are in a second vessel that is separate from the first vessel.

10. A distillation tower that separates a contaminant in a feed stream from a hydrocarbon in the feed stream, the distillation tower comprising:

a stripper section constructed and arranged to separate a feed stream, comprising a contaminant and a hydrocarbon, into an enriched contaminant bottom liquid stream, comprising the contaminant, and a freezing zone vapor stream, comprising the hydrocarbon, at a temperature and pressure at which no solids form; and a controlled freeze zone section constructed and arranged to receive the freezing zone vapor stream from the stripper section and to contact the freezing zone vapor stream with a freezing zone liquid stream at a temperature and pressure at which the a solid, comprising the contaminant, is formed;

wherein the controlled freeze zone section comprises a lower section and an upper section, where the upper section directly abuts and is separate from the lower section, and wherein the controlled freeze zone section further comprises:

a melt tray assembly in the lower section of the controlled freeze zone section that is constructed and arranged to melt a solid, comprising the contaminant, formed in the controlled freeze zone section;

a heating mechanism coupled to at least one of a controlled freeze zone internal surface of a controlled freeze zone vertical wall of the controlled freeze zone section and a controlled freeze zone external surface of the controlled freeze zone vertical wall that at least one of destabilizes and prevents adhesion of the solid to the controlled freeze zone vertical wall, wherein the heating mechanism is above the melt tray assembly and is in the upper section of the controlled freeze zone section.

11. The distillation tower of claim 10, wherein the heating mechanism comprises one of (a) a coil containing a fluid and (b) an electrical conductor, and wherein the distillation tower further comprises a temperature sensor adjacent to the heating mechanism and coupled to the controlled freeze zone internal surface or the controlled freeze zone external surface.

12. The distillation tower of claim 10, wherein the heating mechanism extends around an internal circumference of the controlled freeze zone internal surface or an external circumference of the controlled freeze zone external surface.

13. The distillation tower of claim 10, wherein the heating mechanism comprises a plurality of heating mechanisms, wherein each of the heating mechanisms is coupled to one of the controlled freeze zone internal surface and the controlled freeze zone external surface.

14. The distillation tower of claim 10, wherein the heating mechanism comprises a plurality of heating mechanisms and wherein at least one of the plurality of heating mechanisms is connected to another one of the plurality of heating mechanism.

15. The distillation tower of claim 10, further comprising a rectifier section constructed and arranged to operate at a temperature and pressure at which substantially no solid forms.

16. The distillation tower of claim 15, wherein at least one of the stripping section, the controlled freeze zone section, and the rectifier section are in a first vessel and another of the at least one of the stripping section, the controlled freeze zone section, and the rectifier section are in a second vessel that is separate from the first vessel.

17. The distillation tower of claim 16, wherein the stripping section and the controlled freeze zone section are in the first vessel and the rectifier section is in the second vessel that is separate from the first vessel.

18. A method for producing hydrocarbons comprising:

extracting a feed stream comprising a hydrocarbon and a contaminant from a reservoir;

introducing the feed stream into one of a stripper section and a controlled freeze zone section of a distillation tower;

separating the feed stream in the stripper section into an enriched contaminant bottom liquid stream, comprising the contaminant, and a freezing zone vapor stream, comprising the hydrocarbon, at a temperature and pressure at which no solid forms;

contacting the freezing zone vapor stream in the controlled freeze zone section with a freezing zone liquid stream, comprising the hydrocarbon, at a temperature and pressure at which the freezing zone vapor stream forms a solid, comprising the contaminant, and a hydrocarbon-enriched vapor stream, comprising the hydrocarbon;

accumulating at least a portion of the freezing zone liquid stream in a melt tray assembly in the controlled freeze zone section;

directly applying heat to a controlled freeze zone vertical wall of the controlled freeze zone section with a heating mechanism coupled to at least one of a controlled freeze zone internal surface of the controlled freeze zone vertical wall and a controlled freeze zone external surface of the controlled freeze zone vertical wall, wherein the heating mechanism is coupled to the controlled freeze zone vertical wall above the melt tray assembly;

at least one of destabilizing and preventing adhesion of the solid to the controlled freeze zone vertical wall with the heating mechanism;

removing the hydrocarbon-enriched vapor stream from the distillation tower; and producing the hydrocarbon-enriched vapor stream extracted from the distillation tower.

19. The method of claim 18, wherein the heating mechanism comprises a plurality of heating mechanism and wherein applying heat includes heating separate sections of the controlled freeze zone vertical wall with the heating mechanisms.

20. The method of claim 18, wherein applying heat includes heating the upper section of the controlled freeze zone section.

21. The method of claim 18, wherein the heating mechanism comprises one of (a) a coil containing a fluid and (b) an electrical conductor.

22. The method of claim 18, further comprising detecting a temperature of the heating mechanism with a temperature sensor that is adjacent to the heating mechanism and coupled to at least one of the controlled freeze zone internal surface and the controlled freeze zone external surface.

23. The method of claim 18, further comprising melting or vaporizing the solid at in at least one of a lower section of the controlled freeze zone section and an upper section of the controlled freeze zone section.

24. The method of claim 23, wherein applying heat includes heating the at least one of the lower section and the upper section of the controlled freeze zone section, wherein the lower section directly abuts and is separate from the upper section of the controlled freeze zone section and wherein the upper section directly abuts and is separate from the lower section of the controlled freeze zone section.

25. The method of claim 18, further comprising producing the freezing zone liquid stream in a rectifier section of the distillation tower at a temperature and pressure at which substantially no solid forms.

26. The method of claim 25, wherein at least one of the stripping section, the controlled freeze zone section and the rectifier section are in a first vessel and another of the at least one of the stripping section, the controlled freeze zone section and the rectifier section are in a second vessel that is separate from the first vessel.

* * * * *